(12) United States Patent
Patidar et al.

(10) Patent No.: US 12,128,050 B2
(45) Date of Patent: Oct. 29, 2024

(54) KP372-1-INDUCED DNA DAMAGE AS A CHEMOTHERAPEUTIC APPROACH TO TREAT CANCER

(71) Applicant: New Mexico Tech University Research Park Corporation, Socorro, NM (US)

(72) Inventors: Praveen Patidar, Socorro, NM (US); Talysa Viera, Socorro, NM (US)

(73) Assignee: New Mexico Tech University Research Park Corporation, Socorro, NM (US)

( * ) Notice: Subject to any disclaimer, the term of this patent is extended or adjusted under 35 U.S.C. 154(b) by 0 days.

(21) Appl. No.: 17/523,002

(22) Filed: Nov. 10, 2021

(65) Prior Publication Data

US 2022/0143033 A1 May 12, 2022

Related U.S. Application Data

(60) Provisional application No. 63/111,994, filed on Nov. 10, 2020.

(51) Int. Cl.
*A61K 31/53* (2006.01)

(52) U.S. Cl.
CPC .................................... *A61K 31/53* (2013.01)

(58) Field of Classification Search
CPC .................................................... A61K 31/53
See application file for complete search history.

(56) References Cited

U.S. PATENT DOCUMENTS

| | | | |
|---|---|---|---|
| 2003/0144292 A1* | 7/2003 | Natchus | A61P 35/00 514/561 |
| 2003/0144294 A1 | 7/2003 | Zhang et al. | |
| 2008/0103149 A1 | 5/2008 | Guedat et al. | |
| 2014/0044802 A1 | 2/2014 | Pollard et al. | |

OTHER PUBLICATIONS

Zhao et al., "oNar, a Highly Responsive NAD+/NADH Sensor, Allows High-Throughput Metabolic Screening of Anti-tumor Agents", Cell Metabolism, vol. 21. Issue 5. May 5, 2015, pp. 777-789 (Year: 2015).*
Huang et al., "Leveraging an NQO1 Bioactivatable Drug for Tumor-selective Use of Poly ADP-ribose) Polymerase Inhibitors", Cancer Cell, 2016, vol. 30. (Year: 2016).*
"Talzenna", FDA, Oct. 2018 (Year: 2018).*
Huang X, et al. Leveraging an NQO1 Bioactivatable Drug for Tumor-Selective Use of Poly(ADP-ribose) Polymerase Inhibitors. Cancer Cell. Dec. 1, 20162;30(6):940-952.
PCT/US2021/058765 International Search Report and Written Opinion mailed Feb. 7, 2022.
Jiang, L., et al., "KP372-1-Induced AKT Hyperactivation Blocks DNA Repair to Synergize With PARP Inhibitor Rucaparib via Inhibiting FOXO3a/GADD45a Pathway," Frontiers in Oncology, 2022, pp. 1-15. doi: 10.3389/fonc.2022.976292.
Gerber, D.E., et al., "Phase 1 study of ARQ 761, a B-lapachone analogue that promotes NQO1-mediated programmed cancer cell necrosis," British Journal of Cancer, 2018, vol. 119(8), pp. 928-936.

* cited by examiner

*Primary Examiner* — Andrew D Kosar
*Assistant Examiner* — Gillian A Hutter
(74) *Attorney, Agent, or Firm* — Neal, Gerber & Eisenberg LLP

(57) ABSTRACT

Disclosed herein are methods of treating a cancer that overexpresses NQO1 comprising administering KP372-1. In some embodiments, KP372-1 is administered with a polymerase inhibitor.

20 Claims, 20 Drawing Sheets

KP372-1-INDUCED DNA DAMAGE AS A CHEMOTHERAPEUTIC APPROACH TO TREAT CANCER

CROSS REFERENCE

This application claims the benefit of U.S. Provisional Application No. 63/111,994, filed Nov. 10, 2020, the content of which is incorporated herein by reference in its entirety.

GOVERNMENT RIGHTS

This invention was made with the support of the United States government under Award Number R15GM128071 by the National Institute of General Medical Sciences of the National Institutes of Health. The government has certain rights in the invention.

BACKGROUND

KP372 is a NQO1 redox-cycling agent that induces cytotoxicity in cancer cells by creating a redox imbalance. NAD(P)H:quinone oxidoreductase 1 (NQO1) is a flavoenzyme that catalyzes the two-electron reduction of quinones to hydroquinone forms. NQO1 protein is overexpressed in many solid tumors including pancreatic ductal adenocarcinoma (PDA) and is thought to be a clinical, diagnostic marker of malignancy.

SUMMARY

In some embodiments, disclosed herein is a method for treating a condition, the method comprising: a) administering to a subject in need thereof a therapeutically-effective amount of a compound of Formula (I) or pharmaceutically-acceptable salt thereof or Formula (II) or a pharmaceutically-acceptable salt thereof:

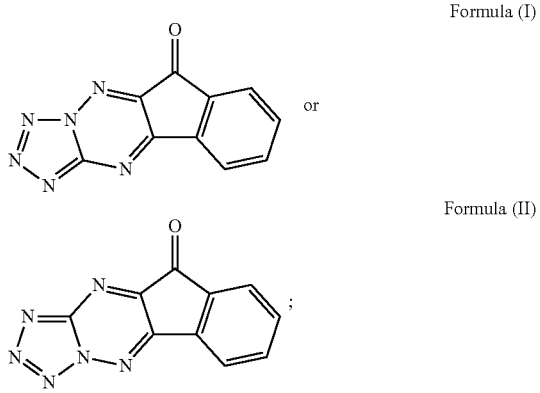

and b) administering to the subject a therapeutically-effective amount of a polymerase inhibitor.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 1C PANEL F BOTTOM PANEL shows quantification of band intensity detected by ImageJ software for NQO1 normalized to α-tubulin of respective sample. Graphs represent means±SEM from n=4. p values were obtained via two-tailed student's t-tests. *, $p<0.05$; , $p<0.01$; *$p<0.001$, comparing pancreatic cancer cell lines with hTERT-HPNE. WB; Western blot.

FIG. 2A PANEL C shows relative survival of siSCR or siNQO1 knockdown cells in the presence of indicated concentrations (μM) of KP372-1±DIC for 2 h. FIG. 2A PANEL D shows clonogenic survival in the presence of various concentrations (μM) of KP372-1±DIC for 2 h. FIG. 2A PANEL E-PANEL F and FIG. 2B PANEL G-PANEL H show relative survival in the presence of various concentrations (μM) of KP372-1±DIC for 2 h. FIG. 2B PANEL K-PANEL L show relative survival in the presence of KP372-1±50 μM DIC and β-lap±50 μM DIC. Graphs represent means±SEM for drug treatment over control (i.e., DMSO) treated (T/C) samples for MIA PaCa-2 n=5 (FIG. 2A PANEL A), Capan-2 n=3 (FIG. 2A PANEL B), MIA PaCa-2±siSCR/siNQO1 n=3 (FIG. 2A PANEL C), MIA PaCa-2: clonogenic survival n=4 (FIG. 2A PANEL D), hTERT-HPNE n=3 (FIG. 2A PANEL E), PANC-1 n=3 (FIG. 2A PANEL F), AsPC-1 n=4 (FIG. 2B PANEL G), and BxPC-3 n=3 (FIG. 2B PANEL H), MIA PaCa-2: time course (FIG. 2B PANEL I), Capan-2: time course n=3 (FIG. 2B PANEL J), MIA PaCa-2: β-lap treatment from n=4 (FIG. 2B PANEL K), and Capan-2: β-lap treatment n=4 (FIG. 2B PANEL L). Each biological replicate was performed in triplicate. p values were obtained via two-tailed student's t-tests. *, $p<0.05$; , $p<0.01$; *, $p<0.001$, comparing KP372-1 alone with KP372-1+DIC or KP372-1+β-lap. For the clonogenic survival assay, p values were obtained via an ordinary one-way ANOVA using the Dunnett's multiple comparisons test. ****, $p<0.0001$; ns, not significant, comparing indicated drug treatments to the DMSO control.

FIG. 3A PANEL A-PANEL D show relative levels of $H_2O_2$ production in control (DMSO), KP 372-1 or KP372-1±50 μM DIC treated cells were measured using the Promega ROS-Glo $H_2O_2$ assay kit. MIA PaCa-2 cells treated, with indicated dose of KP372-1 (μM) for 30 min (FIG. 3A PANEL A), and with 0.2 μM KP372-1 for indicated time (min) points (FIG. 3A PANEL B). Capan-2 cells treated, with indicated dose of KP372-1 (μM) for 30 min (FIG. 3A PANEL C), and with 0.2 μM KP372-1 for indicated time (min) points (FIG. 3A PANEL D).

(FIG. 9A PANEL A-PANEL C) Relative survival measured by MTT assay in the presence of indicated μM concentrations of KP372-1±50 μM dicoumarol (DIC, NQO1 inhibitor), for 2 h. Phenylarsine oxide (PAO) was used as a positive control. Graphs represent % means±S.D. for KP372-1 or DIC or KP372-1+DIC treated over control (i.e., DMSO) treated (T/C) samples for MIA PaCa-2 (FIG. 9A PANEL A), Capan-2 (FIG. 9A PANEL B), and PANC-1 cells (FIG. 9B PANEL C) from n=4, each in triplicate. p values were obtained via an ordinary one-way ANOVA using the Dunnett's multiple comparisons test. , p<0.01; *, p<0.001; ****, p<0.0001; ns, not significant, comparing indicated drug treatments to the DMSO control.

(FIG. 10A PANEL A) Clonogenic survival in the presence of indicated concentrations (μM) of KP372-1±DIC for 2 h. (FIG. 10A PANEL B) Relative levels of $H_2O_2$ production in control (DMSO), KP372-1 and KP372-1±N-acetylcysteine amide (NAC, 1 mM or 5 mM for total of 5 h (pre-treatment for 3 h and co-treatment for 2 h)) treated PANC-1 cells.

DETAILED DESCRIPTION OF THE INVENTION

Figure 1A:
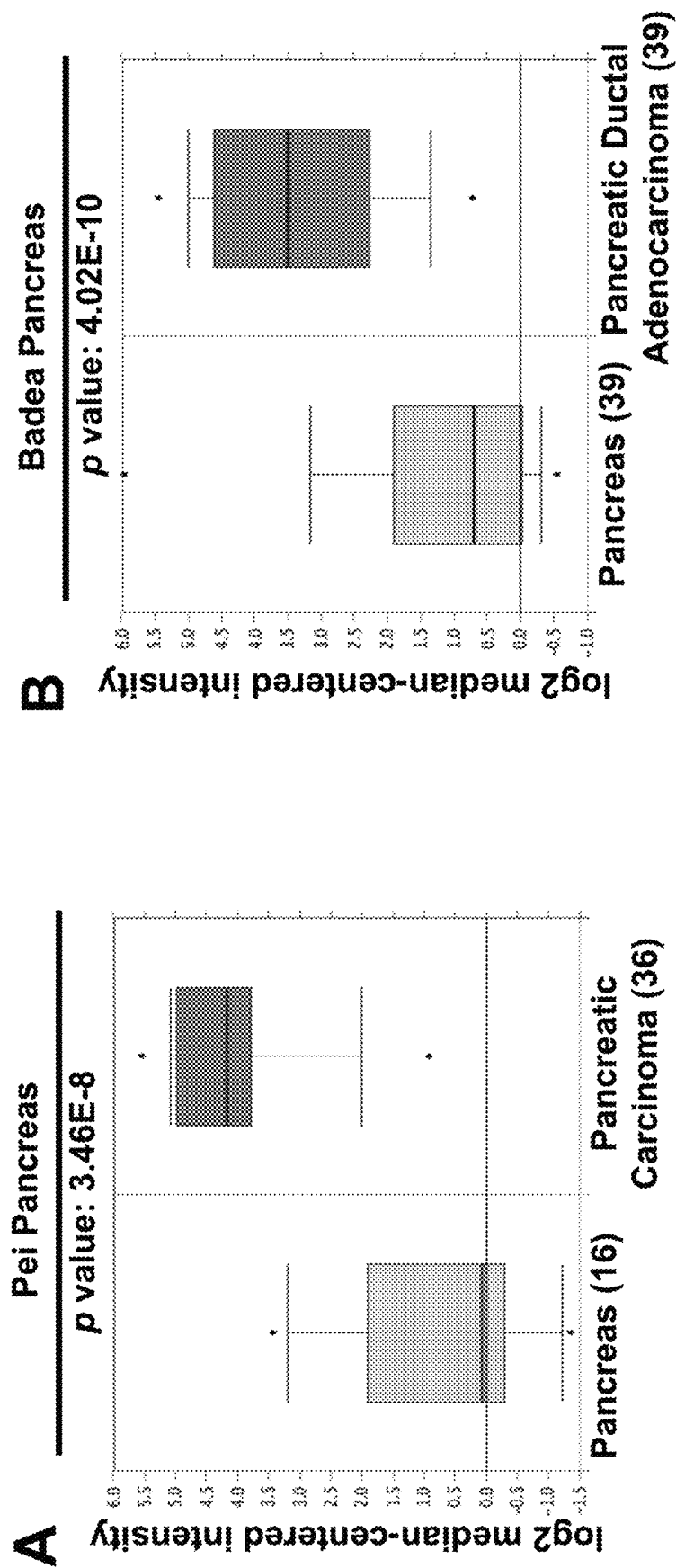
FIG. 1A PANEL A-PANEL B, FIG. 1B PANEL C-PANEL D, and FIG. 1C PANEL D-PANEL E show the upregulation of NQO1 in pancreatic cancer and data retrieved from ONCOMINE displaying changes in NQO1 mRNA levels (log2 median-centered) for pancreatic normal tissue compared to tumor tissue from indicated samples (in parentheses) with p values.

The prognosis for pancreatic cancer is dismal. Potent chemotherapeutic agents that selectively target pancreatic cancer are needed. Elevated expression of NAD(P)H:Quinone Oxidoreductase 1 (NQO1) is frequent in pancreatic cancer. This expression offers promising tumor-selective targeting.

NQO1 is a flavoprotein that functions as a homodimer. Each monomer that is bound to FAD catalyzes an obligatory, two-electron reduction of a wide variety of quinones to the hydroquinone forms using cellular cofactors NADH or NADPH. The hydroquinone forms are unstable, spontaneously react with oxygen, and are converted back to parent quinones. The futile cycle causes significant NAD(P)H oxidation and generates reactive oxygen species (ROS), including superoxides that eventually lead to the formation of hydrogen peroxide ($H_2O_2$). The production of $H_2O_2$ creates oxidative stress and promotes cell death.

The majority of solid cancers including lung, colon, breast, and pancreatic cancer express elevated levels of NQO1. These tumors have significantly lowered Catalase (an $H_2O_2$ detoxifying enzyme) levels. Consequently, the capacity of NQO1 to produce cytotoxic hydroquinones and alter the cellular redox state exclusively in cancer cells is a strategy to target cancers.

β-lapachone (β-lap) is a NQO1 bioactivatable drug. NQO1-dependent redox cycling of β-lap creates ROS that induce DNA damage and hyperactivate the central DNA damage sensor protein poly(ADP-ribose) polymerase 1 (PARP1). Elevated PARP1 activity reduces cellular NAD+ and ATP levels that eventually impede repair of DNA lesions caused by β-lap exposure and ultimately promotes cell death. However, dose-limiting anemia and methemoglobinemia remain challenges with β-lap as a monotherapy or in combination with other agents.

KP372-1 is a NQO1 redox cycling agent that induces cytotoxicity in cancer cells by creating redox imbalance. KP372-1 generates reactive oxygen species (ROS) and exhibits ~10 times greater anti-tumor activity than does β-lap. KP372-1 does not show any toxicity at doses required to produce anti-tumor activity in mice.

In some embodiments, disclosed herein is a method for treating a condition, the method comprising: a) administering to a subject in need thereof a therapeutically-effective amount of a compound of Formula (I) or pharmaceutically-acceptable salt thereof or Formula (II) or a pharmaceutically-acceptable salt thereof:

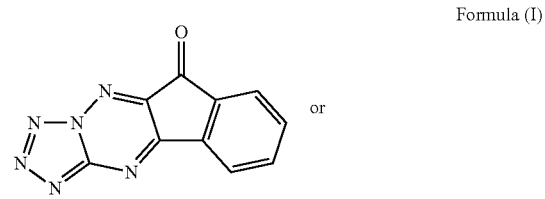 [SMILES: O=C1c2ccccc2-c2nc3nnnn3nc21]

Formula (I)

-continued

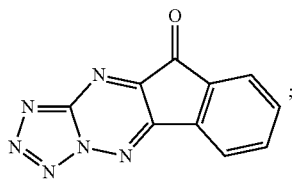
Formula (II)

and b) administering to the subject a therapeutically-effective amount of a polymerase inhibitor.

Therapeutic Agents

Disclosed herein are methods of treating a condition, the method comprising administering a therapeutic agent to a subject in need thereof. In some embodiments, the therapeutic agent is a small molecule. In some embodiments, the therapeutic agent is an antibody. In some embodiments, the therapeutic agent is a protein. In some embodiments, the therapeutic agent is an anti-cancer agent. In some embodiments, the therapeutic agent is a cytotoxic drug. In some embodiments, the therapeutic agent is a cytotoxic drug to treat cancer related to NQO1 anomalies.

In some embodiments, the therapeutic agent is KP372-1, which is a mixture of two isomers in about equal amounts. KP372-1 is a NQO1 redox-cycling agent that induces cytotoxicity in cancer cells by creating a redox imbalance. KP372-1 is ~10-20-fold more potent than β-lapachone, another NQO1 substrate, is against pancreatic cancer cells. In some embodiments, the therapeutic agent is a compound of Formula (I) or a pharmaceutically-acceptable salt thereof or Formula (II) or a pharmaceutically-acceptable salt thereof. In some embodiments, the therapeutic agent is a mixture of a compound of Formula (I) or a pharmaceutically-acceptable salt thereof and a compound of Formula (II) or a pharmaceutically-acceptable salt thereof.

Formula (I)

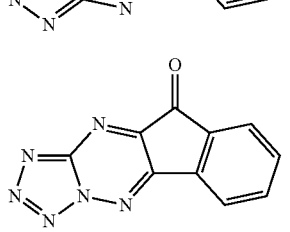

or

Formula (II)

In some embodiments, the therapeutic agent is a mixture of a compound of Formula (I) or a pharmaceutically-acceptable salt thereof and a compound of Formula (II) or a pharmaceutically-acceptable salt thereof in a ratio of about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, or about 1:10. In some embodiments, the ratio is about 1:1. In some embodiments, the ratio is about 2:1. In some embodiments, the ratio is about 1:2.

In some embodiments, a therapeutic agent of the disclosure or a mixture of a compound of Formula (I) or a pharmaceutically-acceptable salt thereof and a compound of Formula (II) or a pharmaceutically-acceptable salt thereof can be administered in an amount of from about 1 mg to about 2,000 mg; from about 100 mg to about 2,000 mg; from about 10 mg to about 2,000 mg; from about 5 mg to about 1,000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

In some embodiments, a therapeutic agent of the disclosure of a mixture of a compound of Formula (I) or a pharmaceutically-acceptable salt thereof and a compound of Formula (II) or a pharmaceutically-acceptable salt thereof can be administered in an amount of about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a therapeutic agent of the disclosure of a mixture of a compound of Formula (I) or a pharmaceutically-acceptable salt thereof and a compound of Formula (II) or a pharmaceutically-acceptable salt thereof can be administered 1, 2, 3, 4, 5, or 6 times a day. In some embodiments, a therapeutic agent of the disclosure of a mixture of a compound of Formula (I) or a pharmaceutically-acceptable salt thereof and a compound of Formula (II) or a pharmaceutically-acceptable salt thereof can be administered once a day. In some embodiments, a therapeutic agent of the disclosure of a mixture of a compound of Formula (I) or a pharmaceutically-acceptable salt thereof and a compound of Formula (II) or a pharmaceutically-acceptable salt thereof can be administered twice a day. In some embodiments, a therapeutic agent of the disclosure of a mixture of a compound of Formula (I) or a pharmaceutically-acceptable salt thereof and a compound of Formula (II) or a pharmaceutically-acceptable salt thereof can be administered three times a day.

The starting dose of a therapeutic agent of the disclosure of a mixture of a compound of Formula (I) or a pharmaceutically-acceptable salt thereof and a compound of Formula (II) or a pharmaceutically-acceptable salt thereof can be about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, or about 1000 mg once daily. Dosing can increase, decrease, remain constant, or a combination thereof throughout the course of treatment. Dosing can be modified (e.g., increased or decreased) by about 5 mg, about 10 mg, about 15 mg, about 20 mg, about 30 mg, about 40 mg, about 50 mg, about 60 mg, about 70 mg, about 80 mg, about 90 mg, about 100 mg, about 200 mg, about 300 mg, about 400 mg, about 500 mg, about 600 mg, about 700 mg, about 800 mg, about 900 mg, or about 1000 mg.

In some embodiments, the methods disclosed herein include co-administering a second therapeutic agent. In some embodiments, the second therapeutic agent is an anti-cancer agent. In some embodiments, the second therapeutic agent is a small molecule. In some embodiments, the second therapeutic agent is an antibody. In some embodiments, the second therapeutic agent is a pathway inhibitor, for example, an inhibitor of at least one polymerase. In some embodiments, the polymerase inhibitor is targeted to inhibit Poly(ADP-ribose) polymerase-1 (PARP-1). In some embodiments, the polymerase inhibitor is a PARP-2 inhibitor. In some embodiments, the polymerase inhibitor is 3-aminobenzamide, 1,5-dihydroxyisoquinolinone, or a tricyclic benzimidazole. In some embodiments, the polymerase inhibitor is talazoparib or a derivative thereof. In some embodiments, the polymerase inhibitor is talazoparib tosylate. In some embodiments, the polymerase inhibitor is rucaparib or a derivative thereof. In some embodiments, the polymerase inhibitor is rucaparib camsylate. In some embodiments, the polymerase inhibitor is olaparib or a derivative thereof. In some embodiments, the polymerase inhibitor is niraparib or a derivative thereof. In some embodiments, the polymerase inhibitor is niraparib tosylate monohydrate. In some embodiments, the polymerase inhibitor is veliparib or a derivative thereof.

In some embodiments, a polymerase inhibitor or a derivative of thereof can be administered in an amount of from about 0.25 mg to about 1 mg. In some embodiments, talazoparib can be administered in an amount of from about 0.25 mg to about 0.5 mg, from about 0.5 mg to about 0.75 mg, or from about 0.75 mg to about 1 mg. In some embodiments, talazoparib can be administered in an amount of about 0.2 mg, about 0.3 mg, about 0.4 mg, about 0.5 mg, about 0.6 mg, about 0.7 mg, about 0.8 mg, about 0.9 mg, or about 1 mg. In some embodiments, a polymerase inhibitor or a derivative of thereof can be administered in an amount of about 0.25 mg. In some embodiments, a polymerase inhibitor or a derivative of thereof can be administered in an amount of about 0.5 mg. In some embodiments, a polymerase inhibitor or a derivative of thereof can be administered in an amount of about 0.75 mg.

In some embodiments, the second therapeutic agent is an agent that enhances cytotoxicity with β-lap. In some embodiments, the second therapeutic agent is an immunotherapy. In some embodiments, the second therapeutic agent is a programmed death 1 (PD-1) monoclonal antibody. In some embodiments, the second therapeutic agent is a programmed death-ligand 1 (PD-L1) monoclonal antibody.

In some embodiments, the immunotherapy can be administered in an amount of about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.5 mg/kg, about 2 mg/kg, about 2.5 mg/kg, about 3 mg/kg, about 3.5 mg/kg, about 4 mg/kg, about 4.5 mg/kg, about 5 mg/kg, about 5.5 mg/kg, about 6 mg/kg, about 6.5 mg/kg, about 7 mg/kg, about 7.5 mg/kg, about 8 mg/kg, about 8.5 mg/kg, about 9 mg/kg, about 9.5 mg/kg, or about 10 mg/kg. In some embodiments, the immunotherapy can be administered in an amount of about 0.1 mg/kg. In some embodiments, the immunotherapy can be administered in an amount of about 1 mg/kg. In some embodiments, the immunotherapy can be administered in an amount of about 3 mg/kg. In some embodiments, the immunotherapy can be administered in an amount of about 5 mg/kg. In some embodiments, the immunotherapy can be administered in an amount of about 10 mg/kg.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg. In some embodiments, the therapeutic agent can be present in a composition in an amount of about 300 mg. In some embodiments, the therapeutic agent can be present in a composition in an amount of about 600 mg. In some embodiments, the therapeutic agent can be present in a composition in an amount of about 1200 mg.

A therapeutic agent described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a therapeutic agent is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

A therapeutic agent disclosed herein can be administered using a scheduled administration cycle. In some embodiments, a therapeutic agent disclosed herein can be administered for 1 day, 2 days, 3 days, 4 days, 5 days, 6 days, 7 days, 8 days, 9 days, 10 days, 11 days, or 12 days. In some embodiments, a therapeutic agent disclosed herein can be administered for 1 day, 2 days, 3 days, 4 days, 5 days, 6 days, 7 days, 8 days, 9 days, 10 days, 11 days, or 12 days over consecutive days. In some embodiments, a therapeutic agent disclosed herein can be administered for 2 consecutive days. In some embodiments, a therapeutic agent disclosed herein can be administered for 3 consecutive days. In some embodiments, a therapeutic agent disclosed herein can be administered for 4 consecutive days. In some embodiments, a therapeutic agent disclosed herein can be administered for 5 consecutive days.

In some embodiments, administration of a therapeutic agent disclosed herein is followed by 1 day, 2 days, 3 days, 4 days, 5 days, 6 days, 7 days, 8 days, 9 days, 10 days, 11 days, or 12 days without administration of a therapeutic agent disclosed herein. In some embodiments, administration of a therapeutic agent disclosed herein is followed by 1 day, 2 days, 3 days, 4 days, 5 days, 6 days, 7 days, 8 days, 9 days, 10 days, 11 days, or 12 days consecutively without administration of a therapeutic agent disclosed herein. In some embodiments, administration of a therapeutic agent disclosed herein is followed by 3 consecutive days without administration of a therapeutic agent disclosed herein. In some embodiments, administration of a therapeutic agent disclosed herein is followed by 4 consecutive days without administration of a therapeutic agent disclosed herein. In some embodiments, administration of a therapeutic agent disclosed herein is followed by 5 consecutive days without administration of a therapeutic agent disclosed herein.

In some embodiments, a therapeutic agent disclosed herein can be administered for a first period of time, followed by no administration of a therapeutic agent disclosed herein for a second period of time. In some embodiments, a therapeutic agent disclosed herein can be administered for 1 day, followed by 6 consecutive days without administration of a therapeutic agent disclosed herein. In some embodiments, a therapeutic agent disclosed herein of the disclosure can be administered for 2 days, followed by 5 consecutive days without administration of a therapeutic agent disclosed herein. In some embodiments, a therapeutic agent disclosed herein can be administered for 3 days, followed by 4 consecutive days without administration of a therapeutic agent disclosed herein. In some embodiments, a therapeutic agent disclosed herein can be administered for 4 days, followed by 3 consecutive days without administration of a therapeutic agent disclosed herein. In some embodiments, a therapeutic agent disclosed herein can be administered for 5 days, followed by 2 consecutive days without administration of a therapeutic agent disclosed herein. In some embodiments, a therapeutic agent disclosed herein can be administered for 6 days, followed by 1 day without administration of a therapeutic agent disclosed herein.

In some embodiments, the periods of administering a therapeutic agent disclosed herein and periods without administration of a therapeutic agent disclosed herein are cycled over a period of 1 week, 2 weeks, 3 weeks, 4 weeks, 5 weeks, 6 weeks, 7 weeks, 8 weeks, 9 weeks, 10 weeks, 11 weeks, or 12 weeks. In some embodiments, the periods of administering a therapeutic agent disclosed herein and periods without administration a therapeutic agent disclosed herein are cycled over a period of 3 weeks. In some embodiments, the periods of administering a therapeutic agent disclosed herein and periods without administration of a therapeutic agent disclosed herein are cycled over a period of 4 weeks. In some embodiments, the periods of administering a therapeutic agent disclosed herein and periods without administration of a therapeutic agent disclosed herein are cycled over a period of 5 weeks. In some embodiments, the periods of administering a therapeutic agent disclosed herein and periods without administration of a therapeutic agent disclosed herein are cycled over a period of 6 weeks.

Pharmaceutically-Acceptable Salts.

The invention provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the invention. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the invention. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the invention. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Compositions of the Invention.

A pharmaceutical composition of the invention can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the invention can be a combination of any therapeutic agents described herein with other chemical components, such as carriers, stabilizers, diluents, dispersing agents, suspending agents, thickening agents, and/or excipients. The pharmaceutical composition facilitates administration of the therapeutic agent to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the therapeutic agent directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active therapeutic agents with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N, N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active therapeutic agents in water-soluble form. Suspensions of the active therapeutic agents can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the therapeutic agents to allow for the preparation of highly concentrated solutions. Alternatively, the active ingredient can be in powder form for constitution with a suitable vehicle, e.g., sterile pyrogen-free water, before use.

In practicing the methods of treatment or use provided herein, therapeutically-effective amounts of the therapeutic agents described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the therapeutic agents used, and other factors. The therapeutic agents can be used singly or in combination with one or more therapeutic agents as components of mixtures.

Pharmaceutical compositions can be formulated using one or more physiologically-acceptable carriers comprising excipients and auxiliaries, which facilitate processing of the active therapeutic agents into preparations that can be used pharmaceutically. Formulations can be modified depending upon the route of administration chosen. Pharmaceutical compositions comprising a therapeutic agent described herein can be manufactured, for example, by mixing, dissolving, emulsifying, encapsulating, entrapping, or compression processes.

The pharmaceutical compositions can include at least one pharmaceutically-acceptable carrier, diluent, or excipient and therapeutic agents described herein as free-base or pharmaceutically-acceptable salt form. Pharmaceutical compositions can contain solubilizers, stabilizers, tonicity enhancing agents, buffers and preservatives.

Methods for the preparation of compositions comprising the therapeutic agents described herein include formulating the therapeutic agents with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a therapeutic agent is dissolved, emulsions comprising a therapeutic agent, or a solution containing liposomes, micelles, or nanoparticles comprising a therapeutic agent as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the invention include liquid, powder, gel, nanosuspension, nanoparticle, microgel, aqueous or oily suspensions, emulsion, and any combination thereof.

Non-limiting examples of pharmaceutically-acceptable excipients suitable for use in the invention include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the invention can be, for example, an immediate release form or a controlled release formulation. An immediate release formulation can be formulated to allow the therapeutic agents to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a therapeutic agent's action for an extended period of time. A delayed release form can be formulated to delay the release of an effective dose of one or more therapeutic agents, for example, for about 4, about 8, about 12, about 16, or about 24 hours.

A controlled release formulation can be a sustained release form. A sustained release form can be formulated to sustain, for example, the therapeutic agent's action over an extended period of time. A sustained release form can be formulated to provide an effective dose of any therapeutic agent described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), each of which is incorporated by reference in its entirety.

Pharmaceutical compositions described herein can be in unit dosage forms suitable for single administration of precise dosages. In unit dosage form, the formulation is divided into unit doses containing appropriate quantities of one or more therapeutic agents. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Therapeutic agents can be delivered via liposomal technology. The use of liposomes as drug carriers can increase the therapeutic index of the therapeutic agents. Liposomes are composed of natural phospholipids, and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Pharmaceutical compositions described herein can be in unit dosage forms suitable for single administration of precise dosages. In unit dosage form, the formulation is divided into unit doses containing appropriate quantities of one or more therapeutic agents. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

Compositions of the invention can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Methods of Use

The present disclosure relates generally to compositions and methods for treating a disease or disorder. In some embodiments, the disease or disorder is associated with NQO1. In one embodiment, a disease or disorder associated with NQO1 is a cell proliferative disease. In some embodiments, the disease or disorder associated with NQO1 is a cell proliferative disease. In some embodiments, therapeutic agents of the invention can be used to treat cancer in a subject.

A therapeutic agent of the invention can, for example, slow the proliferation of cancer cell lines, or kill cancer cells. Non-limiting examples of cancer that can be treated by a method of the disclosure includes one or more leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphomas (Hodgkin's disease, non-Hodgkin's disease), Waldenstrom's macroglobulinemia, heavy chain disease, and solid tumors such as sarcomas and carcinomas (e.g., fibrosarcoma, myosarcoma, liposarcoma, chondrosarcoma, osteogenic sarcoma, chordoma, angiosarcoma, endotheliosarcoma, lymphangiosarcoma, lymphangio endotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms tumor, cervical cancer, uterine cancer, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, schwannoma, meningioma, melanoma, neuroblastoma, and retinoblastoma), or a combination thereof. In some embodiments, the therapeutic agents of the invention show non-lethal toxicity.

In some embodiments, the cell proliferative disease is colorectal cancer. Colorectal cancer is cancer that starts in either the colon or the rectum and is also known as either colon cancer or rectal cancer. In some embodiments, the colorectal cancer is colon adenocarcinoma. In some embodiments, the cell proliferative disease is pancreatic cancer. Pancreatic cancer is cancer that starts in the pancreas. In some embodiments, the pancreatic cancer is pancreatic ductal adenocaricinoma (PDA). In some embodiments, the cell proliferative disease is lung cancer. Lung cancer is cancer that starts in the lungs. In some embodiments, the lung cancer is lung adenocarcinoma. In some embodiments, the cell proliferative disease is breast cancer. Breast cancer is cancer that starts in the breast. In some embodiments, the breast cancer is breast adenocarcinoma. In some embodiments, the cell proliferative disease is liver cancer. Liver cancer is cancer that starts in the liver. In some embodiments, the liver cancer is liver carcinoma.

Therapeutic agents described herein can be administered before, during, or after the occurrence of a disease or condition. The timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A therapeutic agent can be administered as soon as is practical after the onset of a disease or condition is detected or suspected, and for a length of time necessary for the treatment of the disease, such as, for example, from about 1 month to about 3 months. In some embodiments, the length of time a therapeutic agent can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Therapeutic Effects

In some embodiments, the methods of the disclosure can decrease cell proliferation, decrease tumor size, increase overall survival, increase progression free survival, increase percentage of cancer cell death, increase sensitivity to a cancer therapy, or increase a treatment response rate of a therapeutic agent in a subject. In some embodiments, the methods of the disclosure can increase efficacy of the therapeutic agent in a subject compared to a subject treated only with a polymerase inhibitor. In some embodiments, the methods of the disclosure can have a decreased dose of the therapeutic agent compared to a subject treated with the therapeutic agent alone to achieve the same outcome or decrease adverse events associated with the therapeutic agent compared to a subject treated with the therapeutic agent alone.

The methods of the disclosure can decrease cell proliferation in a subject. In some embodiments, the methods of the disclosure can decrease cell proliferation in a subject by from about 5% to about 10%, from about 10% to about 15%, from about 15% to about 20%, from about 20% to about 25%, from about 25% to about 30%, from about 35% to about 40%, from about 40% to about 45%, from about 45% to about 50%, from about 50% to about 75%, from about 75% to about 100%, from about 100% to about 125%, from about 125% to about 150%, from about 150% to about 175%, or from about 175% to about 200% compared to a subject that is not administered a therapeutic agent. In some embodiments, the methods of the disclosure can decrease cell proliferation in a subject by from about 20% to about 25% compared to a subject that is not administered the therapeutic agent. In some embodiments, methods of the disclosure can decrease cell proliferation in a subject by from about 50% to about 75% compared to a subject that is not administered the therapeutic agent.

In some embodiments, methods of the disclosure can decrease cell proliferation in a subject by about 5%, about 10%, about 15%, about 20%, about 25%, about 30%, about 35%, about 40%, about 45%, about 50%, about 75%, about 100%, about 125%, about 150%, about 175%, or about 200% compared to a subject that is not administered the therapeutic agent. In some embodiments, the methods of the disclosure can decrease cell proliferation in a subject by about 20% compared to a subject that is not administered the therapeutic agent. In some embodiments, the methods of the disclosure can decrease cell proliferation in a subject by about 30% compared to a subject that is not administered the therapeutic agent. In some embodiments, the methods of the disclosure can decrease cell proliferation in a subject by about 50% compared to a subject that is not administered the therapeutic agent. In some embodiments, the methods of the disclosure can decrease cell proliferation in a subject by about 70% compared to a subject that is not administered the therapeutic.

In some embodiments, methods of the disclosure can decrease a tumor size in a subject by from about 5% to about 10%, from about 10% to about 15%, from about 15% to about 20%, from about 20% to about 25%, from about 25% to about 30%, from about 35% to about 40%, from about 40% to about 45%, from about 45% to about 50%, from about 50% to about 75%, from about 75% to about 100%, from about 100% to about 125%, from about 125% to about 150%, from about 150% to about 175%, or from about 175% to about 200%. In some embodiments, methods of the disclosure can decrease a tumor size in a subject by from about 20% to about 25%. In some embodiments, methods of the disclosure can decrease a tumor size in a subject by from about 45% to about 50%.

In some embodiments, methods of the disclosure can decrease a tumor size in a subject by about 5%, about 10%, about 15%, about 20%, about 25%, about 30%, about 35%, about 40%, about 45%, about 50%, about 75%, about 100%, about 125%, about 150%, about 175%, or about 200%. In some embodiments, methods of the disclosure can decrease a tumor size in a subject by about 20%. In some embodiments, methods of the disclosure can decrease a tumor size in a subject by about 30%. In some embodiments, methods of the disclosure can decrease a tumor size in a subject by about 50%.

The methods of the disclosure can increase overall survival of a subject. In some embodiments, methods of the disclosure can increase overall survival of a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, methods of the disclosure can increase overall survival of a subject by at least about 10%. In some embodiments, methods of the disclosure can increase overall survival of a subject by at least about 20%. In some embodiments, methods of the disclosure can increase overall survival of a subject by at least about 30%.

Methods of the disclosure can increase progression free survival of a subject. In some embodiments, methods of the disclosure can increase progression free survival of a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, methods of the disclosure can increase progression free survival of a subject by at least about 10%. In some embodiments, methods of the disclosure can increase progression free survival of a subject by at least about 20%. In some embodiments, methods of the disclosure can increase progression free survival of a subject by at least about 30%.

Methods of the disclosure can increase percentage of cancer cell death. In some embodiments, methods of the disclosure can increase percentage of cancer cell death by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, methods of the disclosure can increase percentage of cancer cell death by at least about 10%. In some embodiments, methods of the disclosure can increase percentage of cancer cell death by at least about 20%. In some embodiments, methods of the disclosure can increase percentage of cancer cell death by at least about 30%.

The methods of the disclosure can increase sensitivity to a cancer therapy in a subject. In some embodiments, methods of the disclosure can increase sensitivity to a cancer therapy in a subject by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, methods of the disclosure can increase sensitivity to a cancer therapy in a subject by at least about 10%. In some embodiments, methods of the disclosure can increase sensitivity to a cancer therapy in a subject by at least about 20%. In some embodiments, methods of the disclosure can increase sensitivity to a cancer therapy in a subject by at least about 30%.

The methods of the disclosure can increase a treatment response rate of a therapeutic agent. In some embodiments, methods of the disclosure can increase a treatment response rate of a therapeutic agent by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%. In some embodiments, methods of the disclosure can increase a treatment response rate of a therapeutic agent by at least about 10%. In some embodiments, methods of the disclosure can increase a treatment response rate of a therapeutic agent by at least about 20%. In some embodiments, methods of the disclosure can increase a treatment response rate of a therapeutic agent by at least about 30%.

The methods of the disclosure can increase the efficacy of the therapeutic agent in a subject compared to a subject treated only with the polymerase inhibitor. In some embodiments, methods of the disclosure can increase the efficacy of the therapeutic agent in a subject by at least about at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to a subject treated only with the polymerase inhibitor. In some embodiments, methods of the disclosure can increase the efficacy of the therapeutic agent in a subject by at least about at least about 10% compared to a subject treated only with polymerase inhibitor. In some embodiments, methods of the disclosure can increase the efficacy of the therapeutic agent in a subject by at least about at least about 20% compared to a subject treated only with the polymerase inhibitor. In some embodiments, methods of the disclosure can increase the efficacy of the therapeutic agent in a subject by at least about at least about 30% compared to a subject treated only with the polymerase inhibitor.

The methods disclosed herein can have a decreased dose of the therapeutic agent compared to a subject treated with the therapeutic agent alone to achieve the same outcome. In some embodiments, methods of the disclosure can decrease the required dose of the therapeutic agent by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to a subject treated with the therapeutic agent alone to achieve the same outcome. In some embodiments, methods of the disclosure can decrease the required dose of the therapeutic agent by at least about 10% compared to a subject treated with the therapeutic agent alone to achieve the same outcome. In some embodiments, methods of the disclosure can decrease the required dose of the therapeutic agent by at least about 20% compared to a subject treated with the therapeutic agent alone to achieve the same outcome. In some embodiments, methods of the disclosure can decrease the required dose of the therapeutic agent by at least about 30% compared to a subject treated with the therapeutic agent alone to achieve the same outcome.

The methods disclosed herein can decrease adverse events associated with the therapeutic agent compared to a subject treated with the therapeutic agent alone. In some embodiments, methods of the disclosure can decrease adverse events associated with the therapeutic agent by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% compared to a subject treated with the therapeutic agent alone. In some embodiments, methods of the disclosure can decrease adverse events associated with the therapeutic agent by at least about 10% compared to a subject treated with the therapeutic agent alone. In some embodiments, methods of the disclosure can decrease adverse events associated with the therapeutic agent by at least about 20% compared to a subject treated with the therapeutic agent alone. In some embodiments, methods of the disclosure can decrease adverse events associated with the therapeutic agent by at least about 30% compared to a subject treated with the therapeutic agent alone.

Methods and compositions disclosed herein can be used to increase the effectiveness of treatment with a polymerase inhibitor. In some embodiments, the methods of the disclosure can increase the effectiveness of treatment with an inhibitor of Poly(ADP-ribose) polymerase 1 (PARP1)). In some embodiments, methods of the disclosure can comprise treating a subject with an effective amount of a polymerase inhibitor. In certain embodiments, the effective amount of the polymerase inhibitor is less than 90%, less than 80%, less than 70%, less than 60%, less than 50%, less than 40%, or less than 30% the amount of a polymerase inhibitor monotherapeutic dose compared to when used in combination with a therapeutic agent of the disclosure of a mixture of a compound of Formula (I) or a pharmaceutically-acceptable salt thereof and a compound of Formula (II) or a pharmaceutically-acceptable salt thereof. Alternatively, treatment can be used to reduce the incidence or onset of disease in the subject.

In some embodiments, methods and compositions disclosed herein allow for less frequent administration of a polymerase inhibitor. Thus, the disclosure provides a method for treating a disease or disorder associated with NQO1, comprising administering to a subject in need thereof an effective amount of the pathway inhibitor (e.g., a polymerase inhibitor) and an effective amount of a modulator of glucose metabolism, wherein the pathway inhibitor is administered less frequently than the frequency effective in the absence of treatment with the modulator of glucose metabolism.

EXAMPLES

Example 1: NQO1 Expression is Elevated in Pancreatic Cancer

NQO1 is a prototypical target gene for a transcription factor, nuclear factor erythroid 2 p45-related factor 2 (Nrf2).

In response to increased oxidative stress, Nrf2 binds to a DNA sequence known as antioxidant response element (ARE) to upregulate downstream target genes, including NQO1.

To determine the suitability of NQO1 as a potential target against pancreatic cancer, the Oncomine database was utilized to evaluate NQO1 expression. Within the database, multiple studies reported significantly elevated NQO1 mRNA levels, ranging from 3-10-fold, in pancreatic cancer compared to normal pancreatic tissue from a considerable number of patients (FIG. 1A PANEL A-PANEL B, FIG. 1B PANEL C-PANEL D, and FIG. 1C PANEL E). Overall, 109 pancreatic cancer specimens showed significantly higher levels of NQO1 expression compared to 70 normal pancreatic tissue (a total of 179 specimens).

To strengthen the suitability of NQO1 as a promising target against pancreatic cancer, NQO1 protein levels were evaluated in five different commonly utilized model pancreatic cancer cell lines and one non-cancerous, immortalized pancreatic duct cell line, hTERT-HPNE. MIA PaCa-2, Capan-2 and AsPC-1 showed significantly higher NQO1 protein levels compared to hTERT-HPNE (FIG. 1C PANEL F). BxPC-3 showed a similar NQO1 level to that of hTERT-HPNE, and PANC-1 did not show any detectable NQO1 expression (FIG. 1C PANEL F). The absence of detectable level of NQO1 protein in PANC-1 cells was consistent with a previous study reporting a polymorphism in NQO1 gene leading to enhanced susceptibility of expressed NQO1 to proteasome-mediated degradation in these cells. Collectively, data presented in FIGS. 1A-1C suggest that elevated NQO1 levels offer a promising target for therapeutic intervention against pancreatic cancer.

Example 2: Elevated NQO1 Expression Sensitizes Pancreatic Cancer Cells to KP372-1

Figure 1B:
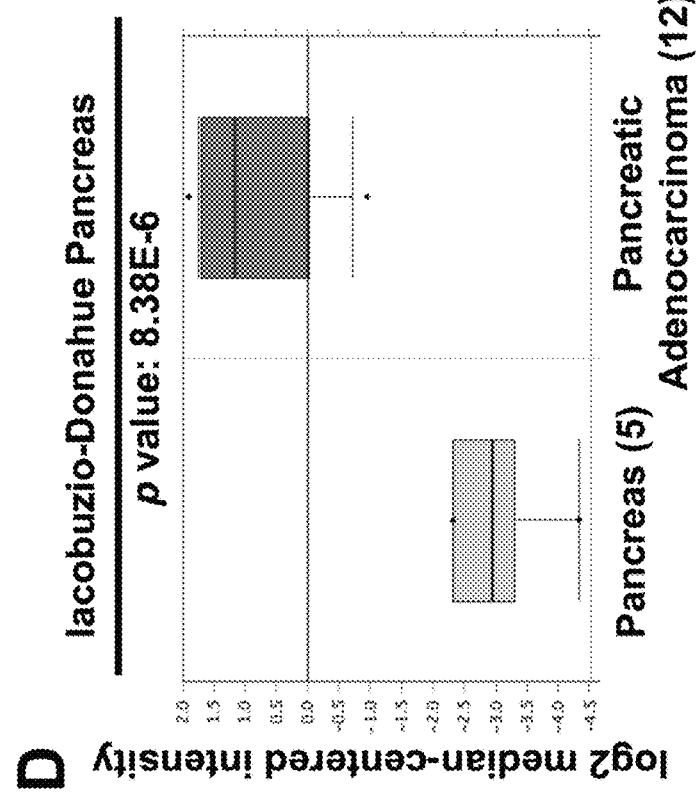
FIG. 1C PANEL F TOP PANEL shows a representative image of Western blot analyses for NQO1 protein level in frequently utilized pancreatic cancer cell lines along with non-cancerous pancreatic duct cells (hTERT-HPNE). α-Tubulin was used as a protein loading control.
Figure 1B:
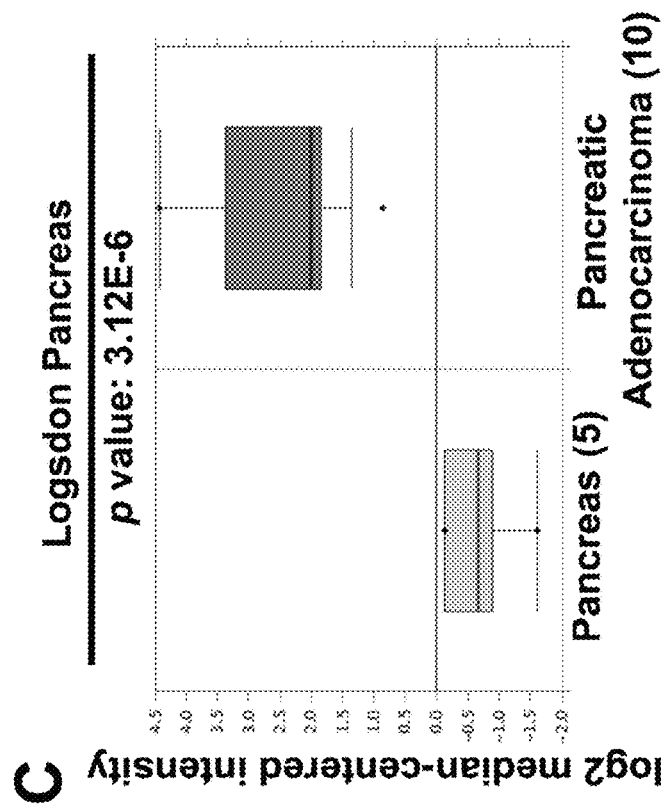
Figure 1C:
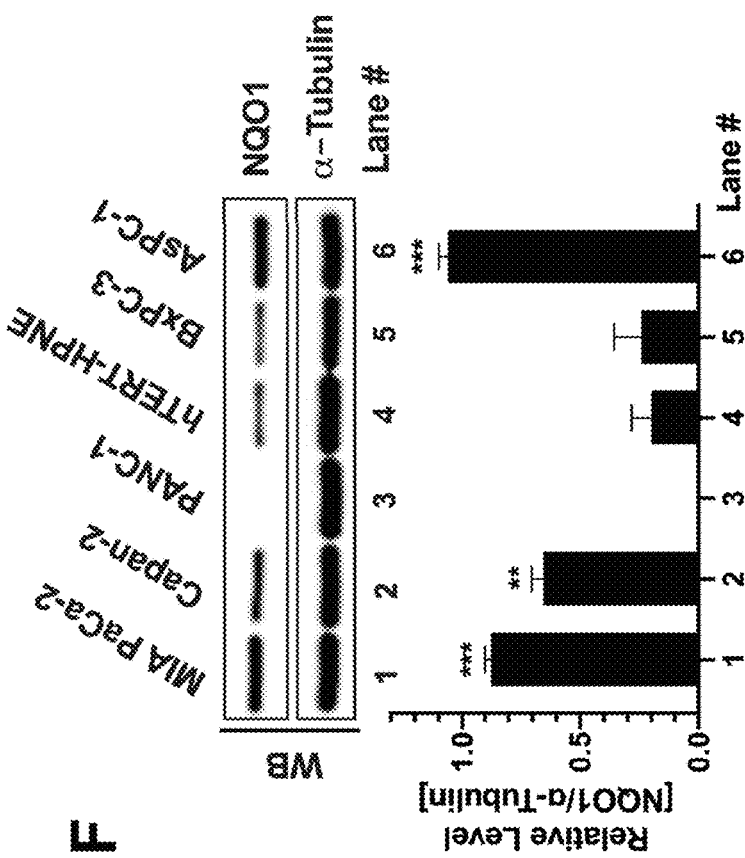
Figure 1C:
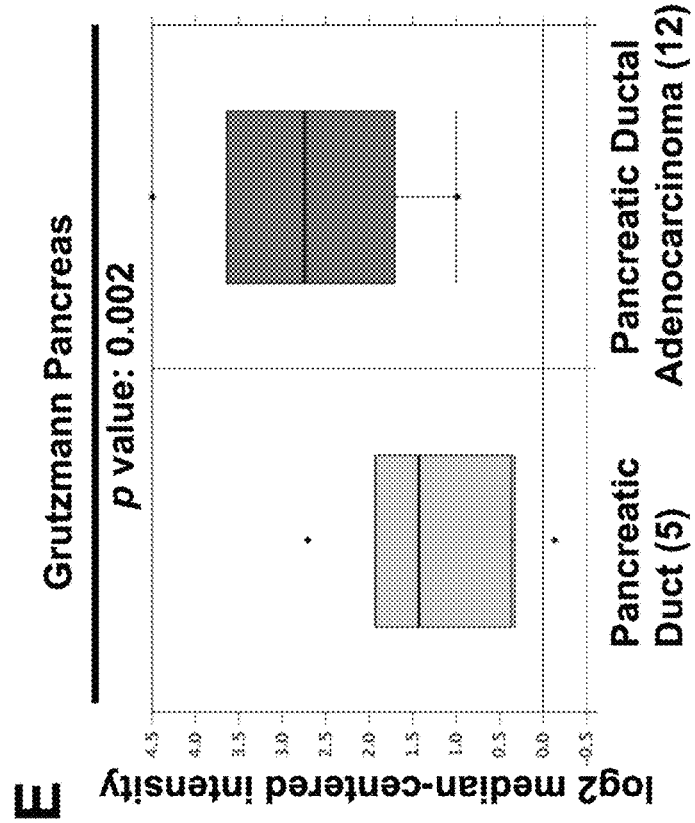
Figure 2A:
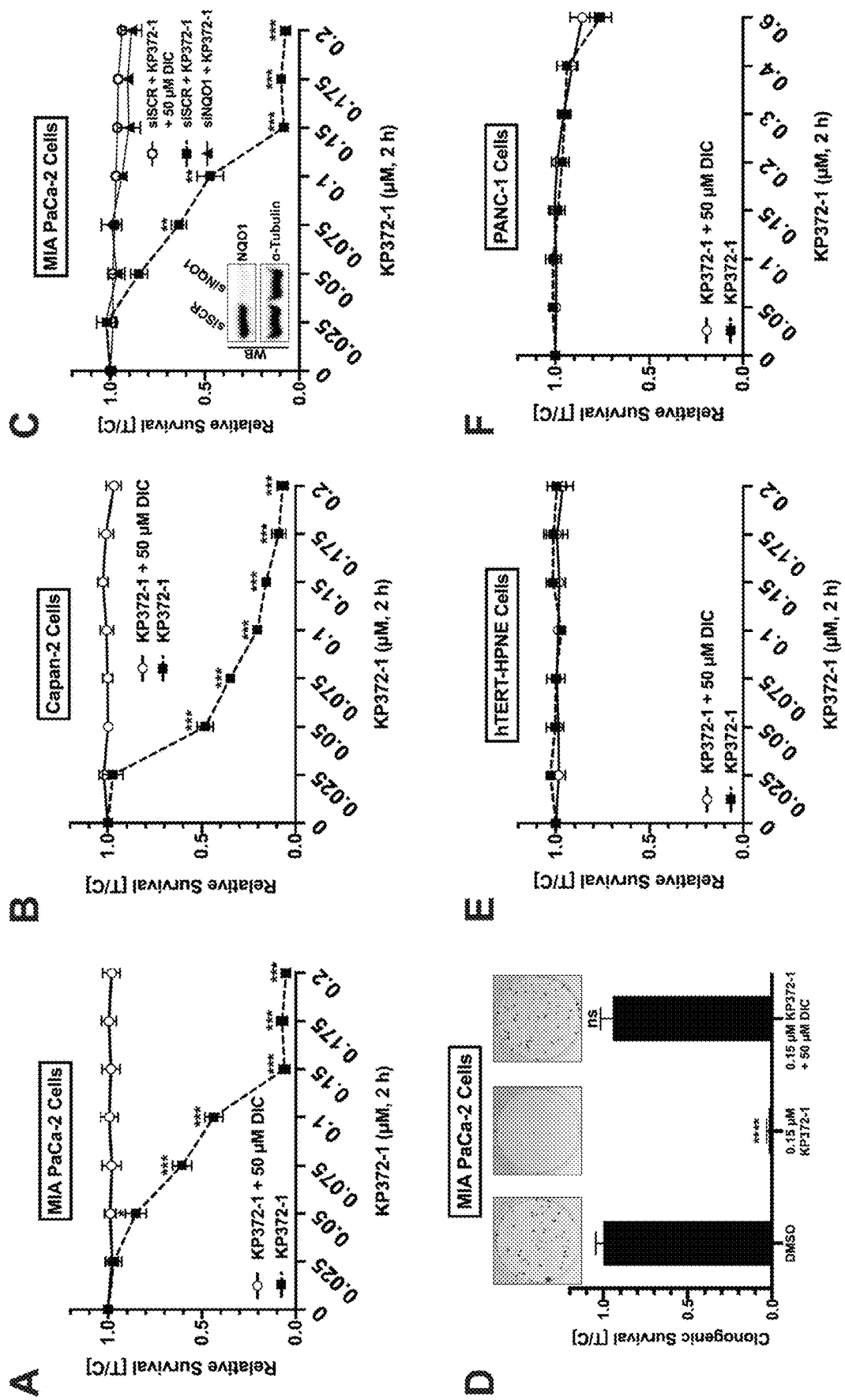
FIG. 2A PANEL A-PANEL F and FIG. 2B PANEL G-PANEL L show that elevated NQO1 expression sensitizes pancreatic cancer cells to KP372-1. Relative survival was measured by DNA content assay in the presence of varying concentrations (μM) of KP372-1±dicoumarol (DIC, NQO1 inhibitor) for 2 h.
Figure 2B:
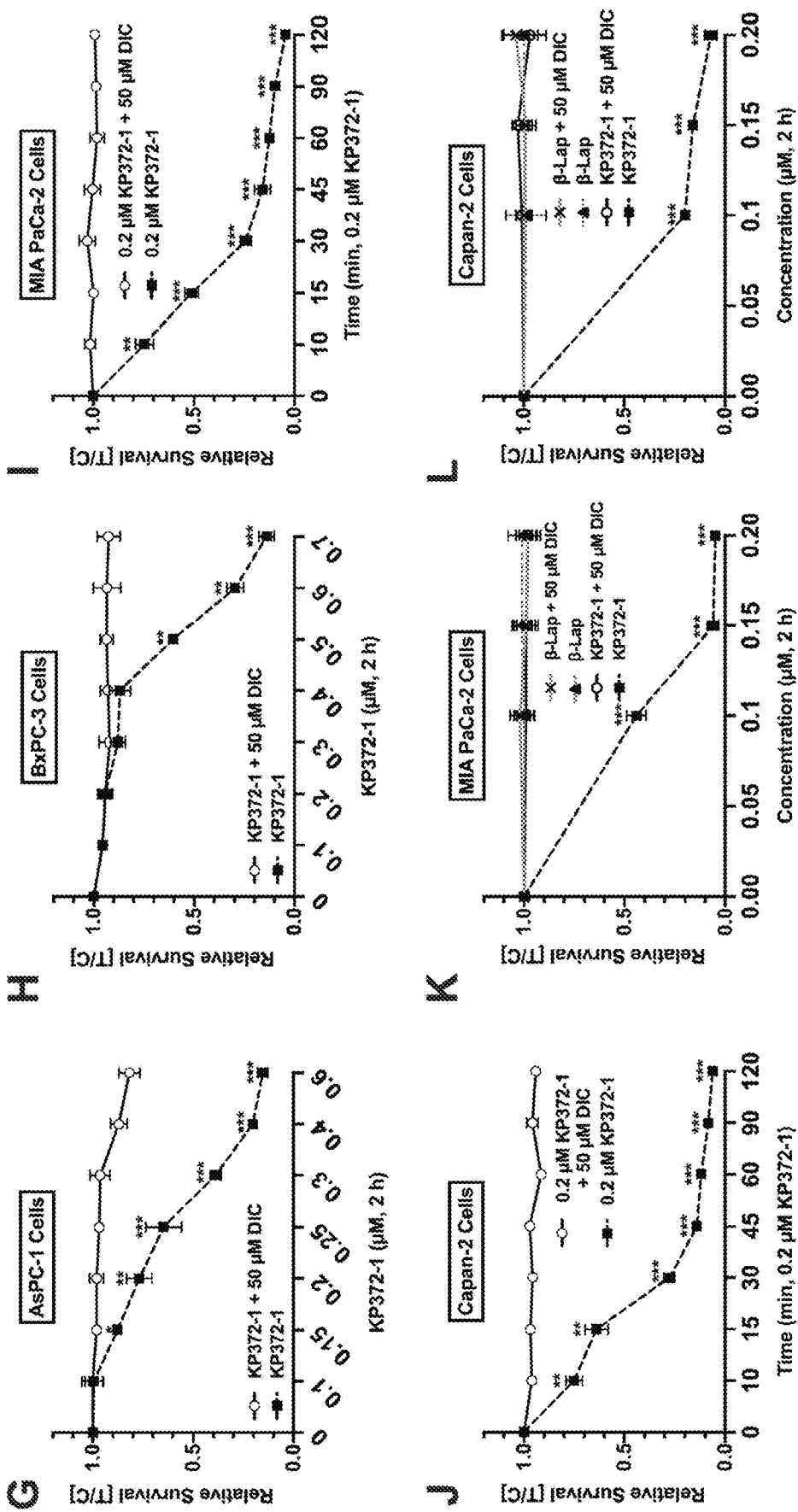
FIG. 2B PANEL I-PANEL J show relative survival in the presence of 0.2 μM concentration of KP372-1±50 μM DIC for indicated time points.
Figure 9A:
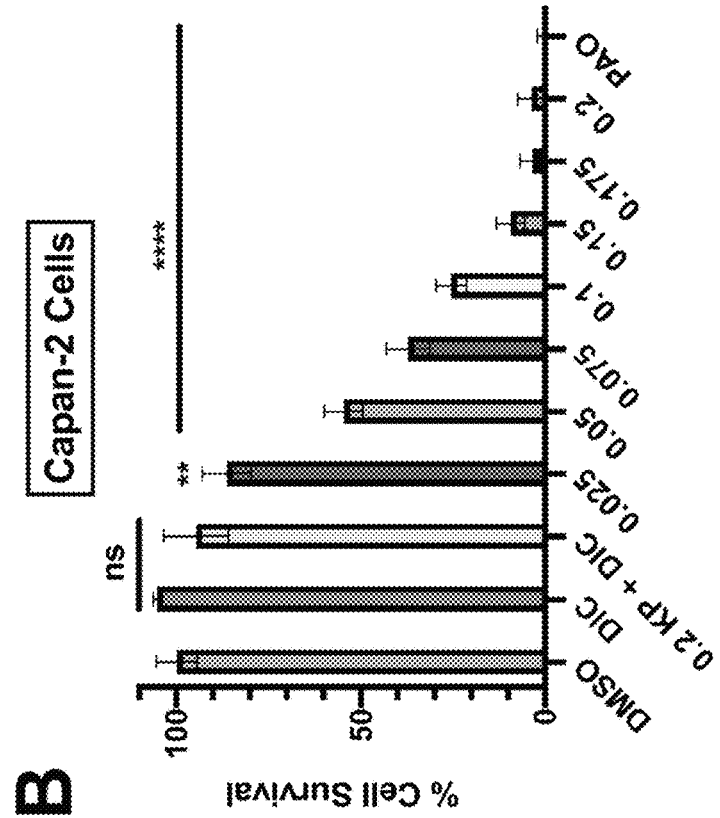
FIG. 9A PANEL A-PANEL B and FIG. 9B PANEL C-PANEL E show the sensitivity of β-lapachone (β-lap) against pancreatic cancer cells.
Figure 9A:
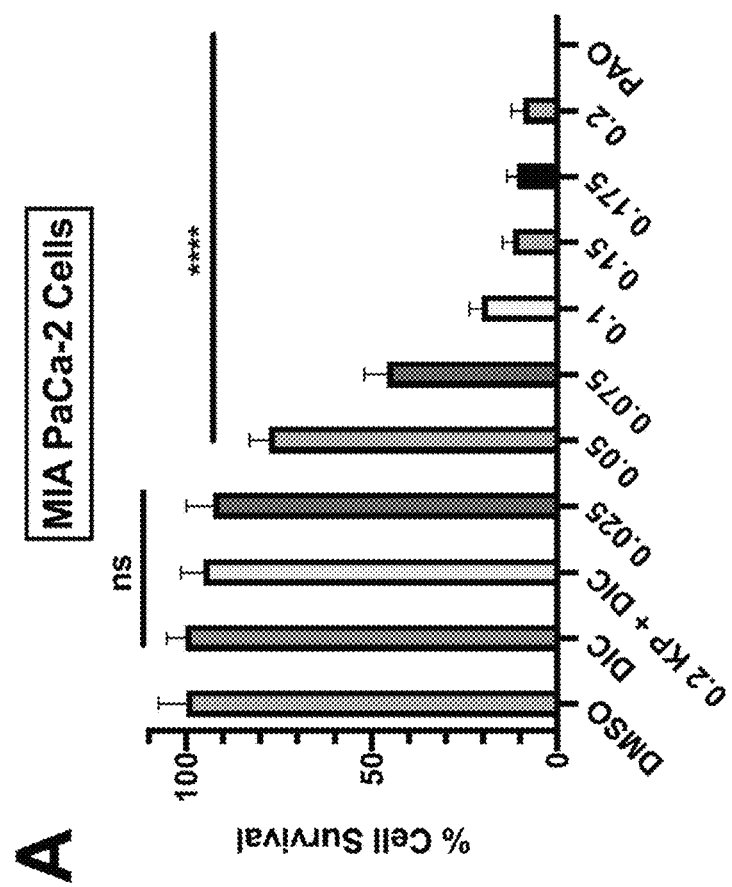

The cytotoxicity induced by KP372-1 was systematically evaluated against a panel of pancreatic cancer cell lines mentioned in FIGS. 1A-1C via the DNA content assay. MIA PaCa-2 and Capan-2, two frequently used pancreatic cancer model cell lines, showed robust toxicity with 2 h exposure to KP372-1 where concentrations as low as 0.05 µM caused significant cell death and a concentration of 0.2 µM led to >95% cell death (FIG. 2A PANEL A and PANEL B, respectively). Dicoumarol (DIC), an inhibitor of NQO1, rescued these cells completely from cytotoxic effects of KP372-1 (FIG. 2A PANEL A-PANEL B). The siRNA-mediated transient knockdown of NQO1 reversed the sensitivity of MIA PaCa-2 cells against KP372-1 and provided genetic evidence that KP372-1-induced cytotoxicity is NQO1-dependent (FIG. 2A PANEL C). Similar to the DNA content assay, the clonogenic survival and MTT assays provided additional validation of robust toxicity induced by KP372-1 against pancreatic cancer cells that can be rescued by DIC (FIG. 2A PANEL D, FIG. 9A PANEL A, FIG. 9A PANEL B). Similar KP372-1 treatment conditions did not elicit cell death in the immortalized normal pancreatic duct cell line, hTERT-HPNE (FIG. 2A PANEL E). PANC-1 cells with no detectable level of NQO1 protein also did not show appreciable toxicity (FIG. 2A PANEL F, FIG. 9B PANEL C, FIG. 10A, PANEL A). AsPC-1 and BxPC-3 cells showed significant toxicity at >0.15 µM and at >0.5 µM KP372-1 (FIG. 2B PANEL G, FIG. 2B PANEL H). Despite having high levels of NQO1, the sensitivity of AsPC-1 cells was lower compared to MIA PaCa-2 (FIG. 1C PANEL F and FIG. 2A PANEL A). This result was likely due to the ~2.5 times higher antioxidant capacity of AsPC-1 cells compared to MIA PaCa-2 cells.

Figure 9B:
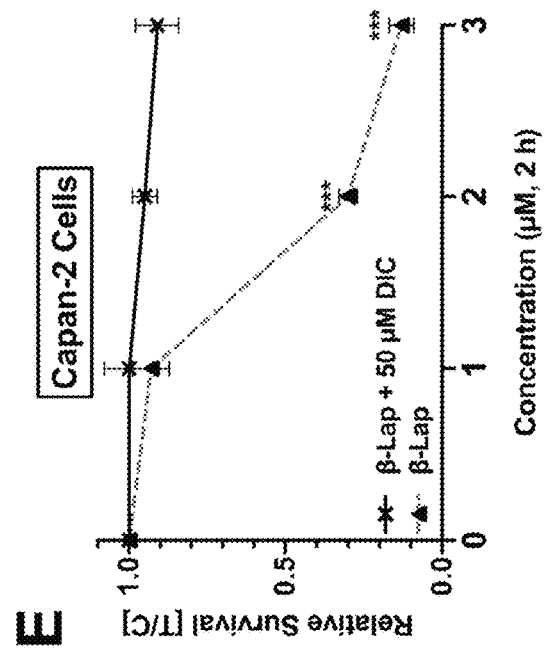
(FIG. 9B PANEL D-PANEL E) Relative survival measured by DNA content assay in the presence of indicated μM concentrations of β-lap±50 μM dicoumarol (DIC, NQO1 inhibitor), for 2 h. Graphs represent means±SEM for β-lap treated over control (i.e., DMSO) treated (T/C) samples for MIA PaCa-2 (A), Capan-2 (B) cells from n=4, each in triplicate. p values were obtained via two-tailed student's t-tests. *, p<0.05; p<0.01; *p<0.001, comparing β-lap with β-lap+DIC.
Figure 9B:
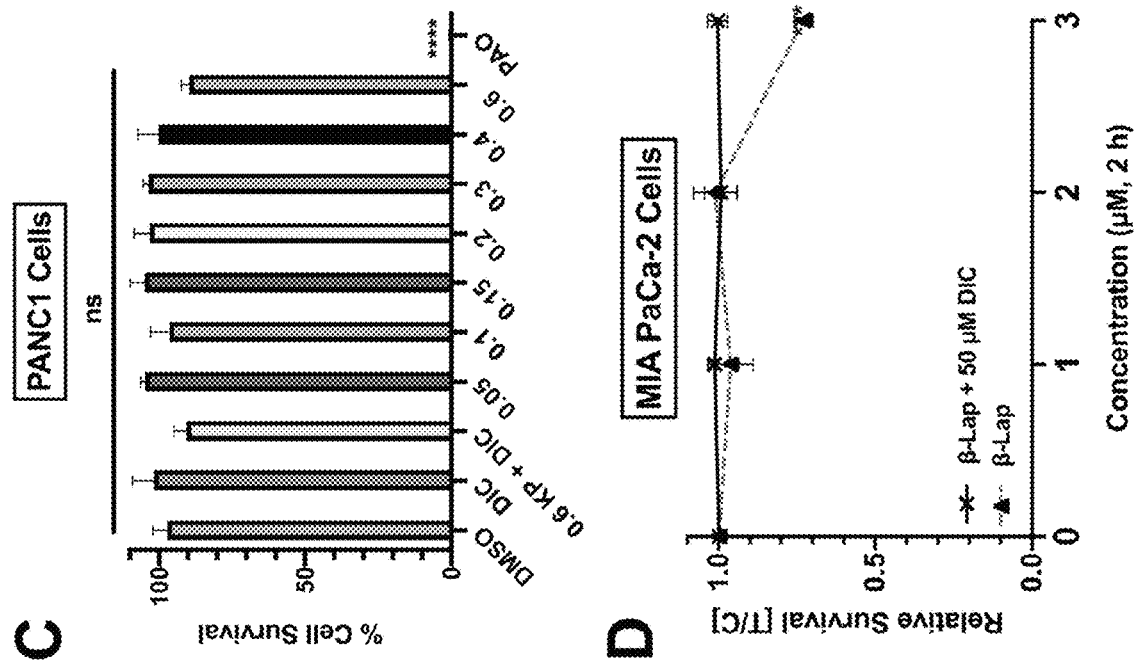

Finally, to determine the minimum time of exposure required to induce cell death, a time-course experiment for MIA PaCa-2 and Capan-2 with 0.2 µM KP372-1 was conducted. A 10 min exposure was sufficient to induce significant cell death, whereas 2 h exposure led to >95% cell death in MIA PaCa-2 and Capan-2 (FIG. 2I-J, respectively). Toxicities of KP372-1 with β-lapachone (β-lap) were compared against some of the pancreatic cancer cells. For MIA PaCa-2 cells, β-lap did not induce appreciable toxicity up to 2.0 µM, whereas, 0.2 µM KP372-1 was lethal for these cells (FIG. 2B PANEL K and FIG. 9B PANEL D). For Capan-2 cells, β-lap did not induce appreciable toxicity up to 1.0 µM, whereas, 0.2 µM KP372-1 was lethal for these cells (FIG. 2B PANEL L and FIG. 9B PANEL E). These data show that KP372-1 was much more potent (at least ~10- to 20-fold) than β-lap was against pancreatic cancer cells. The data suggest that the potent redox cycling agent KP372-1 selectively induces cell death in NQO1-expressing pancreatic cancer cells and spares non-cancerous immortalized pancreatic duct cells.

Example 3: KP372-1 Treatment Enhances ROS Production in Pancreatic Cancer Cells

Figure 3A:
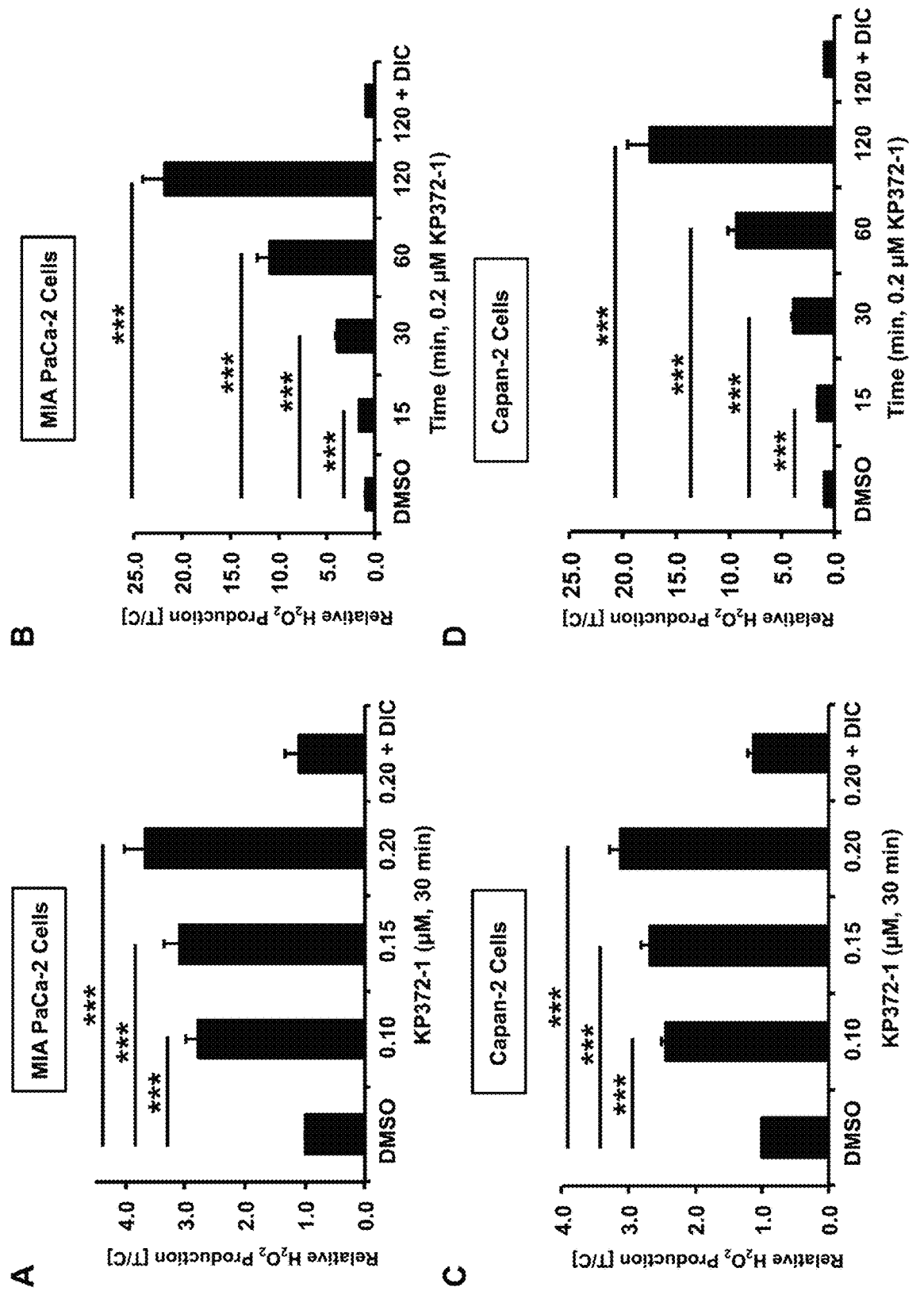
FIG. 3A PANEL A-PANEL D and FIG. 3B PANEL E-PANEL F show that KP372-1 treatment enhances ROS production in pancreatic cancer cells.
Figure 3B:
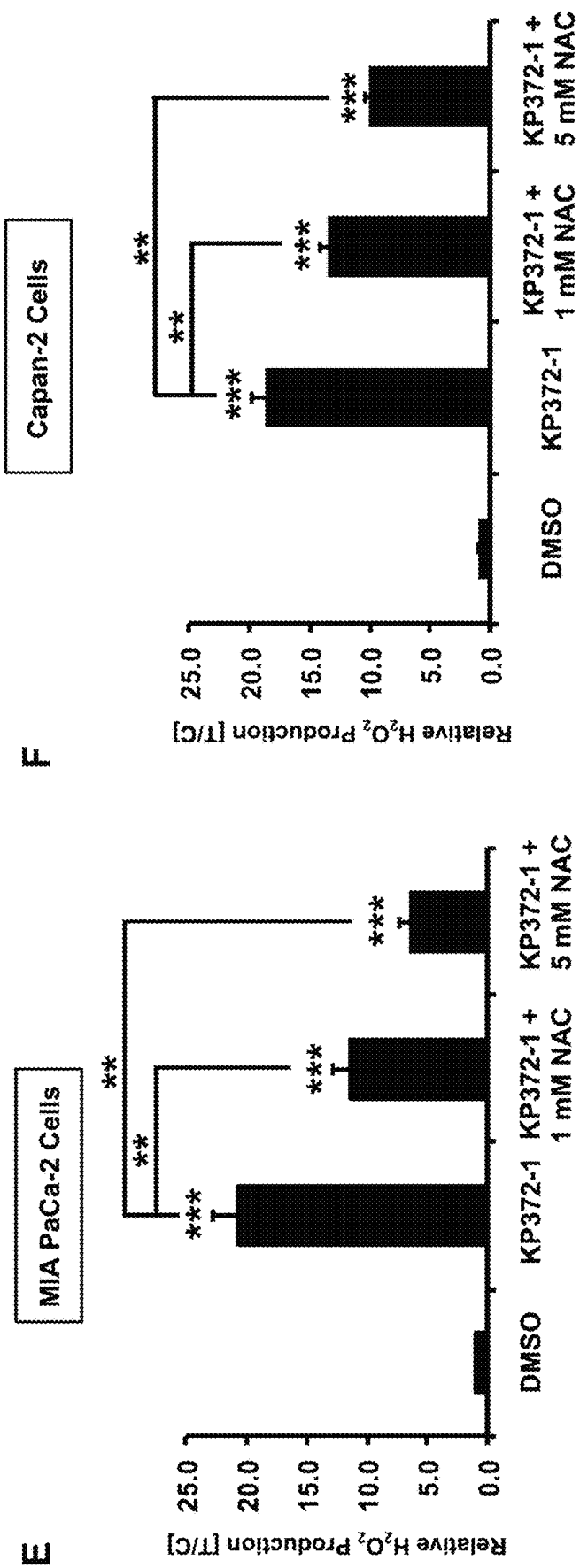
FIG. 3B PANEL E-PANEL F show relative levels of $H_2O_2$ production in control (DMSO), KP372-1 and KP372-1±N-acetylcysteine amide (NAC, 1 mM or 5 mM for total of 5 h (pre-treatment for 3 h and co-treatment for 2 h)) treated MIA PaCa-2 cells (FIG. 3B PANEL E) or Capan-2 cells (FIG. 3B PANEL F) with indicated concentrations. Bar graphs represent means±SEM for treated/control samples from n=4, each performed in duplicate. p values were obtained via two-tailed student's t-tests. *, $p<0.05$; $p<0.01$; *$p<0.001$, comparing treated with control samples.
Figure 10A:
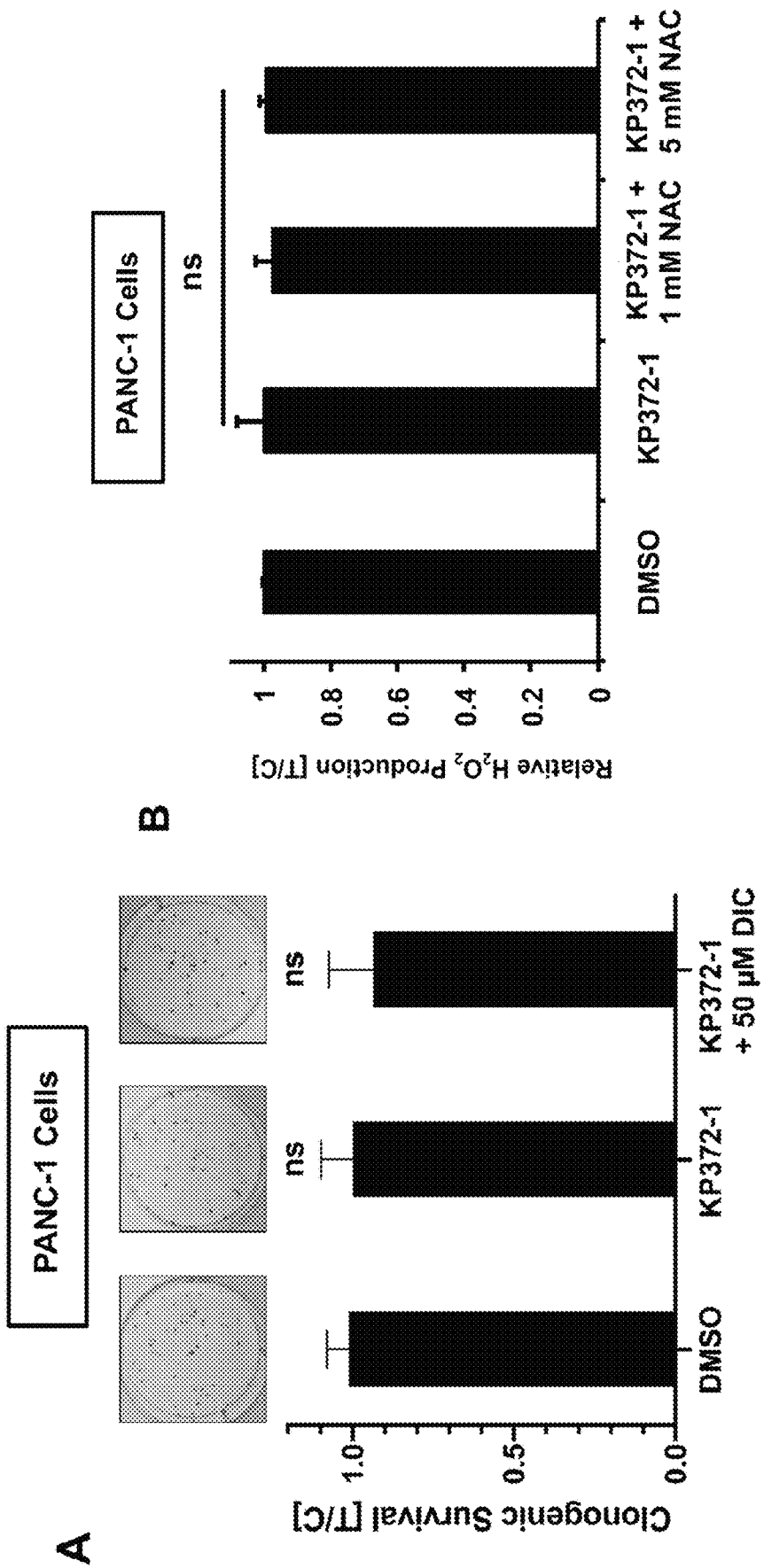
FIG. 10A PANEL A-PANEL B, FIG. 10B PANEL C, and FIG. 10C PANEL D-PANEL E show that PANC-1 cells are resistant to KP372-1 treatment.

To define systematically the mechanistic basis of cytotoxicity, the production of ROS due to NQO1 redox cycling of KP372-1 was evaluated in pancreatic cancer cells. Specifically, $H_2O_2$ formation was measured in MIA PaCa-2 and Capan-2 cells, and dose-response and time-course studies were performed. Compared to control (DMSO treatment), 30 min exposure of indicated concentrations (µM) of KP372-1 caused significant enhancement of $H_2O_2$ production in MIA PaCa-2 cells, whereas co-treatment of KP372-1+DIC rescued ROS formation to control levels (FIG. 3A PANEL A). Next, a time course response with indicated KP372-1 concentrations (µM) was performed, and $H_2O_2$ production was found to be dramatically enhanced by 2 h treatment in MIA PaCa-2 cells (FIG. 3A PANEL B). To further validate KP372-1-induced $H_2O_2$ production, dose and time-course studies were performed using Capan-2 cells, which showed similar enhancement of $H_2O_2$ formation in the cells (FIG. 3A PANEL C and PANEL D, respectively). Finally, a well-known ROS scavenger, N-acetylcysteine amide (NAC), was used to rescue KP372-1-induced ROS production in pancreatic cancer cells. NAC significantly rescued ROS production in a dose-dependent manner in both MIA PaCa-2 and Capan-2 cells treated with KP372-1 (FIG. 3B PANEL E and PANEL F, respectively). KP372-1 treatment did not elicit ROS production above background levels in NQO1-deficient PANC-1 cells (FIG. 10A PANEL B). Together, these data support high levels of ROS production in NQO1-expressing pancreatic cancer cells after KP372-1 treatment.

Example 4: KP372-1 Elicits Robust DNA Damage in Pancreatic Cancer Cells

Figure 4:
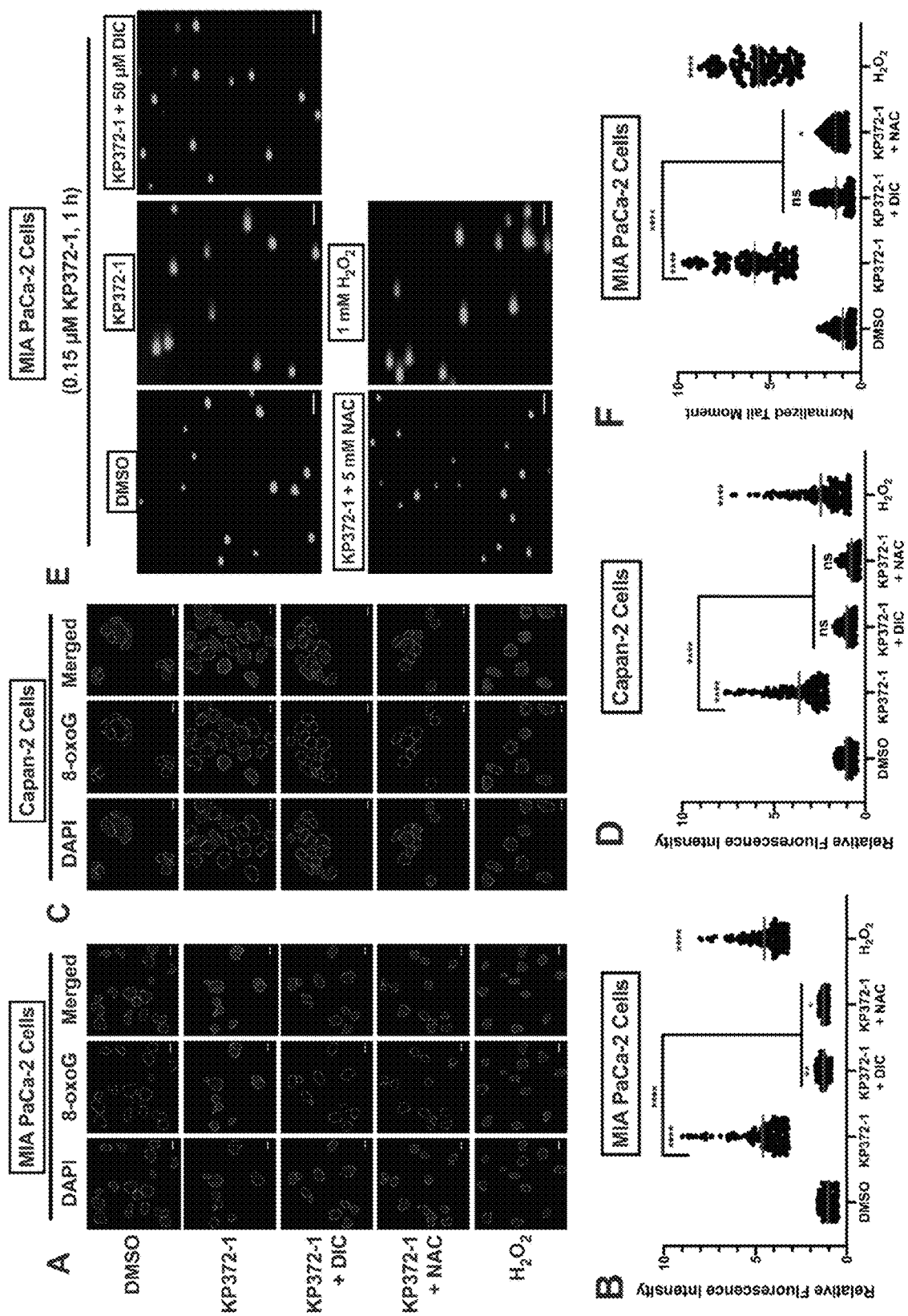
FIG. 4 PANEL A-PANEL F show that KP372-1 treatment instigates oxidative DNA damage and DNA breaks in pancreatic cancer cells. PANEL A-PANEL D show relative levels of nuclear 8-oxoG signal in control (DMSO), 0.15 μM KP372-1, 0.15 μM KP372-1±50 μM DIC or KP372-1±N-acetylcysteine amide (NAC, 5 mM for total of 4 h (pre-treatment for 3 h and co-treatment for 1 h)) treated cells were measured by immunofluorescence confocal microscopy. Representative images of MIA PaCa-2 cells (PANEL A), and quantification of fluorescence signal (PANEL B). Representative images of Capan-2 cells (PANEL C), and quantification of fluorescence signal (PANEL D). Cells treated with $H_2O_2$ (1 mM, 15 min in 1×PBS) served as positive control. The scale bar represents 10 μm. Graphs represent the means (red bar) for treated/control samples from n=3, each performed in duplicate for total of 150 cells. Relative fluorescence intensities were determined by ImageJ software (version 1.53c, imagej.net). PANEL E-PANEL F show relative levels of comet tail moment of control (DMSO), 0.15 μM KP372-1±50 μM DIC or KP372-1±N-acetylcysteine amide (NAC, 5 mM for total of 4 h (pre-treatment for 3 h and co-treatment for 1 h)) treated cells measured by confocal microscopy. Representative images of MIA PaCa-2 cells (PANEL E), and quantification of fluorescence signal (PANEL F). Cells treated with $H_2O_2$ (1 mM, 15 min in 1×PBS) served as positive control. The scale bar represents 10 μm. Tail moments were obtained using the ImageJ plug-in OpenComet v1.3. Graphs represent the means for treated/control samples from n=3, each performed in duplicate for total of 150 cells. p values were obtained via an ordinary one-way ANOVA using the Dunnett's multiple comparisons test. *, $p<0.05$; , $p<0.01$; **$p<0.0001$; ns, not significant, comparing indicated drug treatments to the DMSO control.

The increase in ROS level in pancreatic cancer cells suggested that KP372-1 might cause DNA damage, including DNA breaks. Direct oxidative DNA damage induced by KP372-1 treatment was studied by measuring 8-oxoguanine (8-oxoG) levels detected by 8-oxoG specific antibodies via immunofluorescence confocal microscopy. MIA PaCa-2 cells showed robust 8-oxoG signal after 0.15 µM KP372-1 exposure for 1 h compared to control (DMSO-treated) cells, and treatment with DIC or the ROS scavenger NAC significantly reduced the 8-oxoG levels instigated by KP372-1, comparable to control levels (FIG. 4 PANEL A and PANEL B). MIA PaCa-2 cells treated with $H_2O_2$ were used as a positive control (FIG. 4 PANEL A and PANEL B).

Figure 10B:
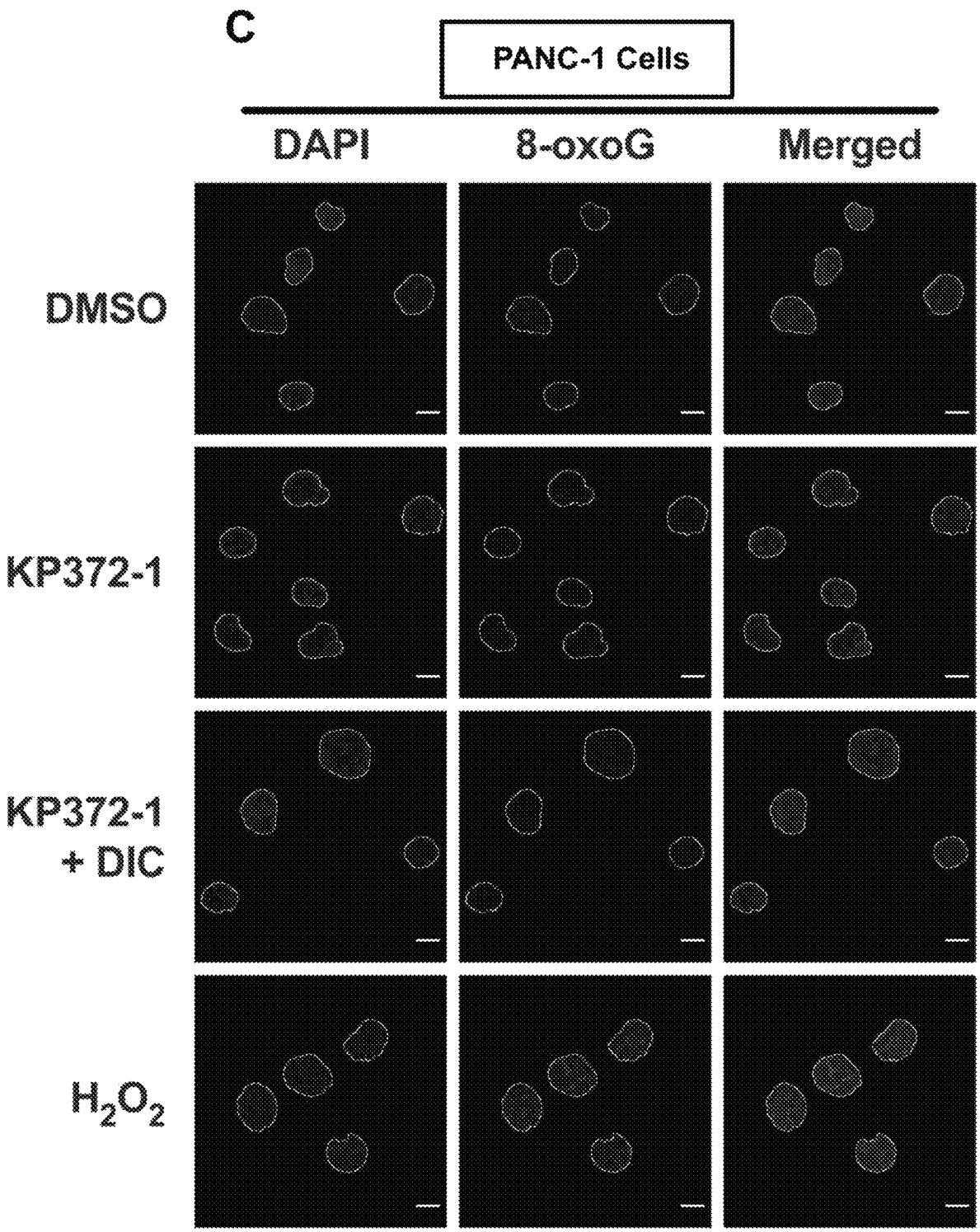
(FIG. 10B PANEL C-PANEL D) Relative levels of nuclear 8-oxoG signal in control (DMSO), 0.15 μM KP372-1, or 0.15 μM KP372-1±50 μM DIC treated for 1 h were measured by immunofluorescence confocal microscopy. Cells treated with $H_2O_2$ (1 mM, 15 min in 1×PBS) served as positive control. Representative images of PANC-1 cells (FIG. 10B PANEL C), and quantification of fluorescence signal (FIG. 10C PANEL D). The scale bar represents 10 μm. Graphs represent the means (red bar) for treated/control samples from n=3, each performed in duplicate for total of 150 cells. p values were obtained via an ordinary, one-way ANOVA using the Dunnett's multiple comparisons test. ****, p<0.0001; ns, not significant, comparing indicated drug treatments to the DMSO control.
Figure 10C:
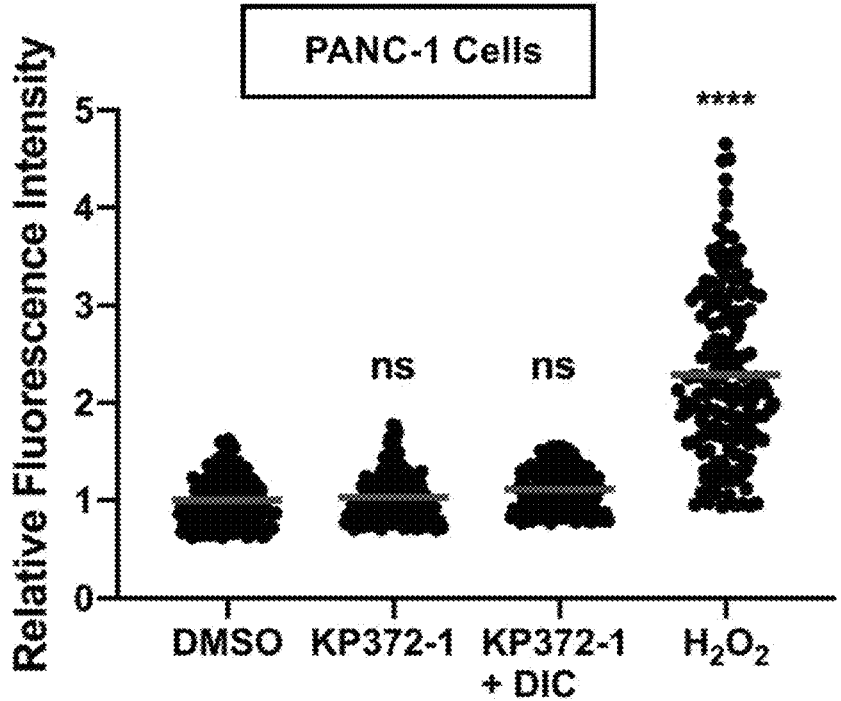
(FIG. 10C PANEL E) Assessment of phosphorylated H2AX (7H2AX) and PAR (poly-(ADP-ribose)) via Western blotting as a marker of DNA damage response induced by KP372-1. MIA PaCa-2 cells treated with 0.15 μM KP372-1±50 μM DIC for indicated time (min) points.
Figure 10C:
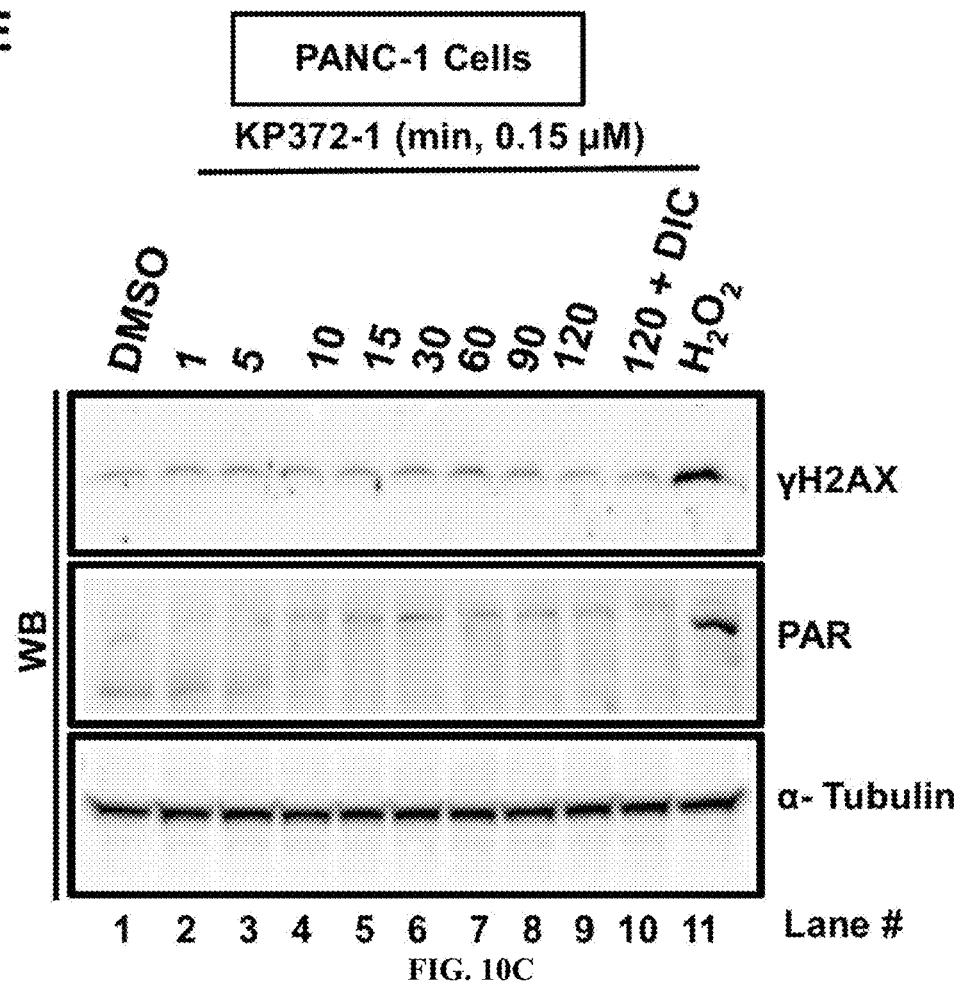

To support further the 8-oxoG formation, similar studies were carried out in Capan-2 cells. A strong induction of 8-oxoG signal was observed by KP372-1 treatment that was rescued by DIC or NAC treatment (FIG. 4 PANEL C and PANEL D). KP372-1 treatment did not cause an increase in 8-oxoG signal above background levels in NQO1-deficient PANC-1 cells (FIG. 10B PANEL C and FIG. 10C PANEL D). These data support oxidative DNA damage instigated by KP372-1 in NQO1-expressing pancreatic cancer cells.

Next, the induction of DNA double strand breaks (DSBs) after KP372-1 treatment was studied by utilizing the neutral comet assay. MIA PaCa-2 cells treated with 0.15 µM of KP372-1 for 1 h showed significantly elevated comet tail moments compared to control (DMSO-treated) cells (FIG. 4 PANEL E and PANEL F). Importantly, treatment of DIC or NAC significantly reduced the comet tail moment of KP372-1-treated cells (FIG. 4 PANEL E and PANEL F). MIA PaCa-2 cells treated with $H_2O_2$ served as positive control (FIG. 4 PANEL E and PANEL F). These data show that KP372-1 treatment induces DSBs in NQO1-expressing pancreatic cancer cells.

Figure 5A:
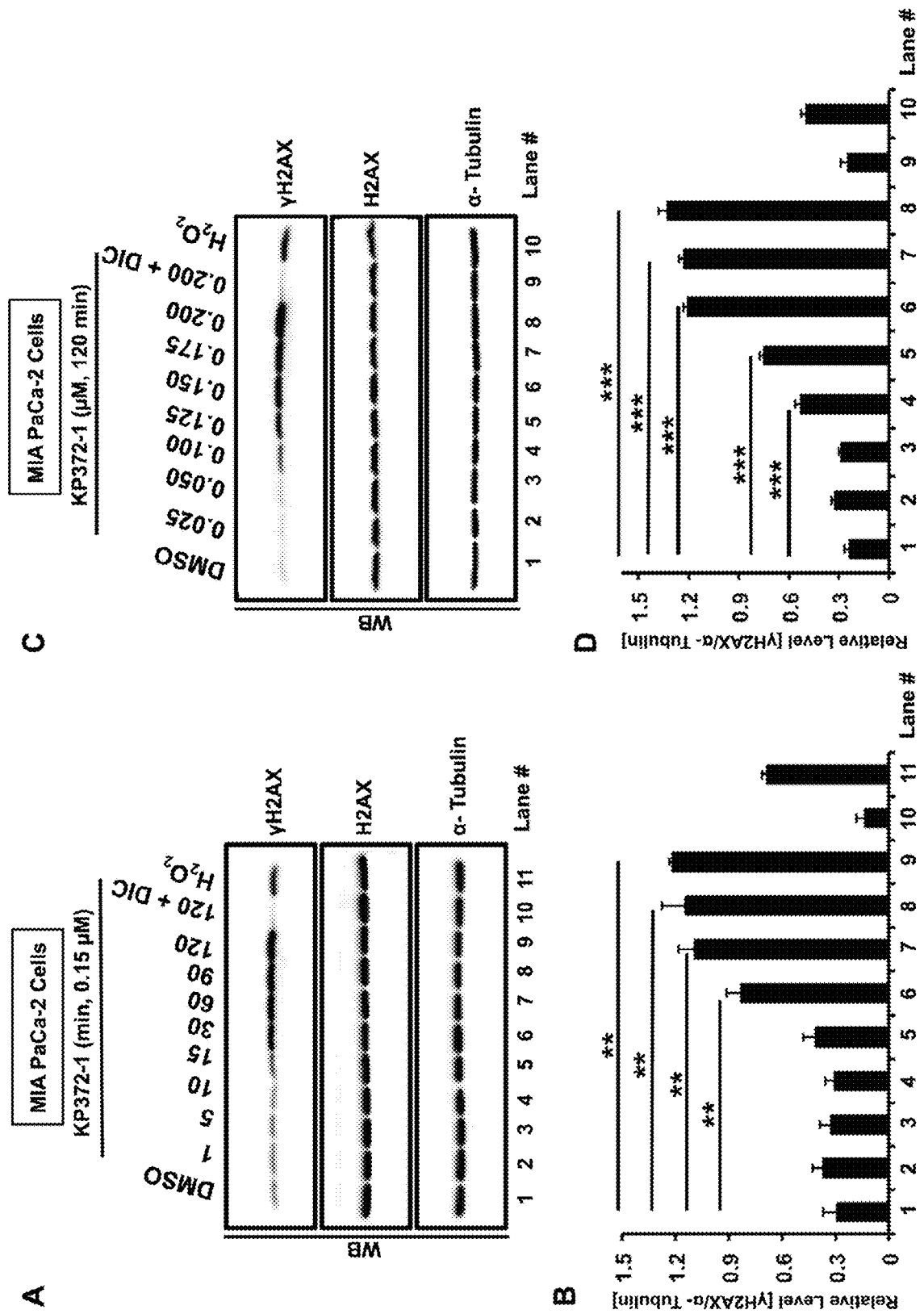
FIG. 5A PANEL A-PANEL D and FIG. 5B PANEL E-PANEL H show that KP372-1 elicits robust DNA damage signaling in pancreatic cancer cells, and provide assessment of phosphorylated H2AX (γH2AX) via Western blotting as a marker of DNA damage response induced by KP372-1. MIA PaCa-2 cells treated with 0.15 μM KP372-1±50 μM DIC for indicated time (min) points (FIG. 5A PANEL A-PANEL B), blot image and quantification, respectively, and with indicated dose of KP372-1 (μM)±50 μM DIC for 120 min (FIG. 5A PANEL C-PANEL D), blot image and quantification, respectively. Capan-2 cells treated with 0.15 μM KP372-1±50 μM DIC for indicated time (min) points (FIG. 5B PANEL E-PANEL F), blot image and quantification, respectively, and with indicated dose of KP372-1 (μM)±50 μM DIC for 120 min (FIG. 5B PANEL G-PANEL H), blot image and quantification, respectively. Representative Western blot images are presented. Bar graphs represent quantification of band intensities (means±SEM) of γH2AX normalized to α-tubulin of respective sample from n=5. Band intensities were detected by ImageJ software (version 1.53c, imagej.net) and α-tubulin was used as loading control. Cell lysates prepared from $H_2O_2$-treated cells (1 mM, 15 min in 1×PBS) served as positive control. p values were obtained via two-tailed student's t-tests. *, $p<0.05$; , $p<0.01$; *$p<0.001$, comparing treated with control (DMSO) samples. WB; Western blot.
Figure 5B:
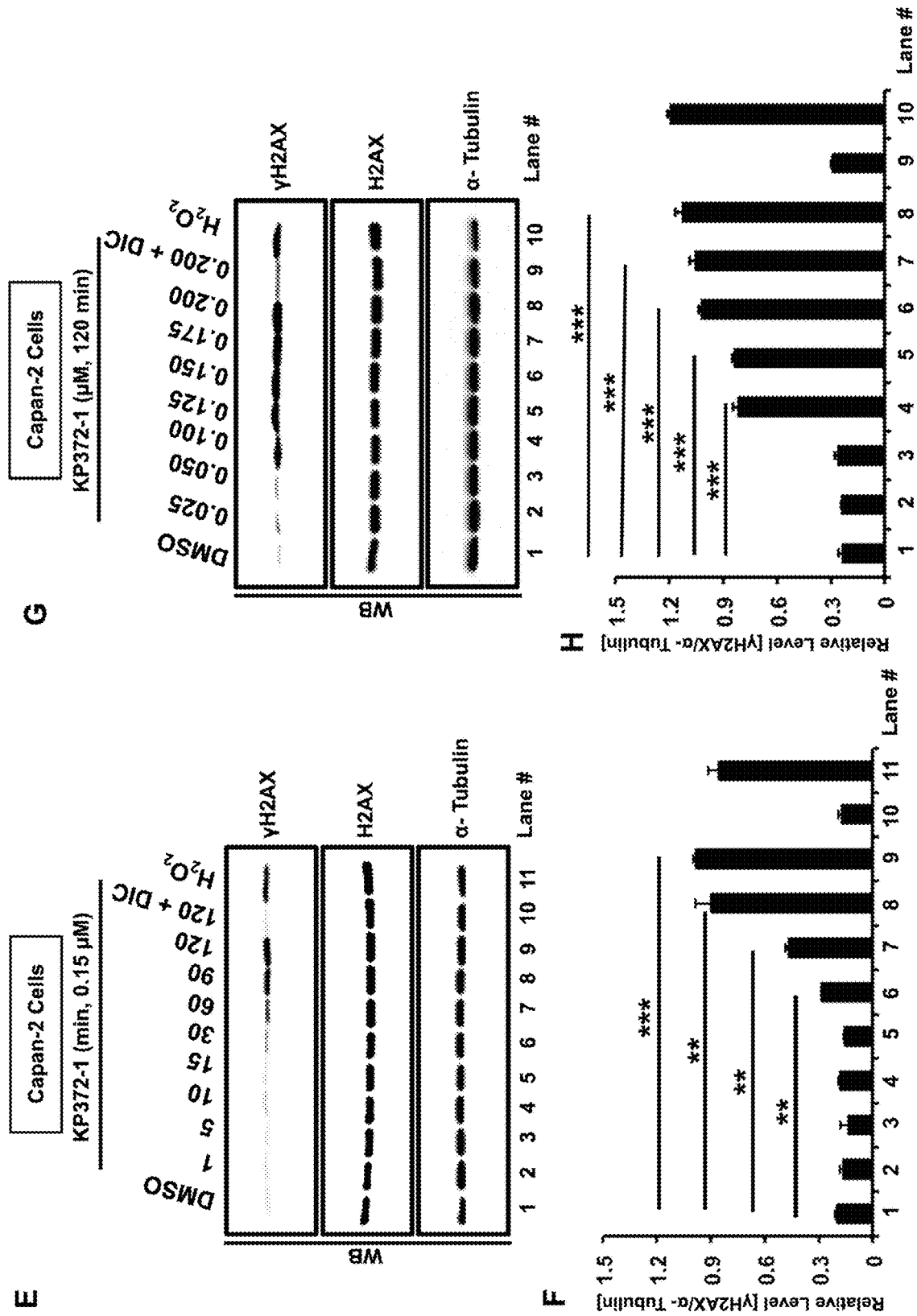

To provide additional validation, time-course and dose-response studies were carried out to evaluate alteration in phosphorylated H2AX (7H2AX) level using Western blotting as a proxy of DSB formation and concomitant signaling after KP372-1 treatment. Cell lysate from $H_2O_2$ treated cells were utilized as positive control. A significant level of DNA damage was observed at multiple time points within a 2 h window in MIA PaCa-2 cells treated with 0.15 µM KP372-1 compared to control (DMSO treated) samples, where co-treatment with DIC eliminated DNA damage (FIG. 5A PANEL A and PANEL B). Next, dose-response experiments were carried out with 2 h of KP372-1 treatment. A dose-dependent enhancement of DNA damage was observed (FIG. 5A PANEL C and PANEL D). To validate further DNA damage induction by KP372-1 treatment, similar studies were carried out in Capan-2 cells. Clear time- and dose-dependent induction of DNA damage was observed in Capan-2 cells (FIG. 5B PANEL E-PANEL H) similar to that of MIA PaCa-2 cells. Similar treatment of NQO1-deficient PANC-1 cells did not show increased yH2AX signal above background levels (FIG. 10B PANEL E). Collectively, these data show that a robust DNA damage response is instigated by KP372-1 in NQO1-expressing pancreatic cancer cells.

Example 5: KP372-1 Hyperactivates PARP1 in Pancreatic Cancer Cells

Mechanistically, reactive oxygen species produced by NQO1-dependent redox cycling of KP372-1 cause robust DNA damage, including DNA breaks. Further, KP372-1-induced DNA damage hyperactivates the central DNA damage sensor protein poly(ADP-ribose) polymerase 1 (PARP1) and activates caspase-3 to initiate cell death.

Figure 6:
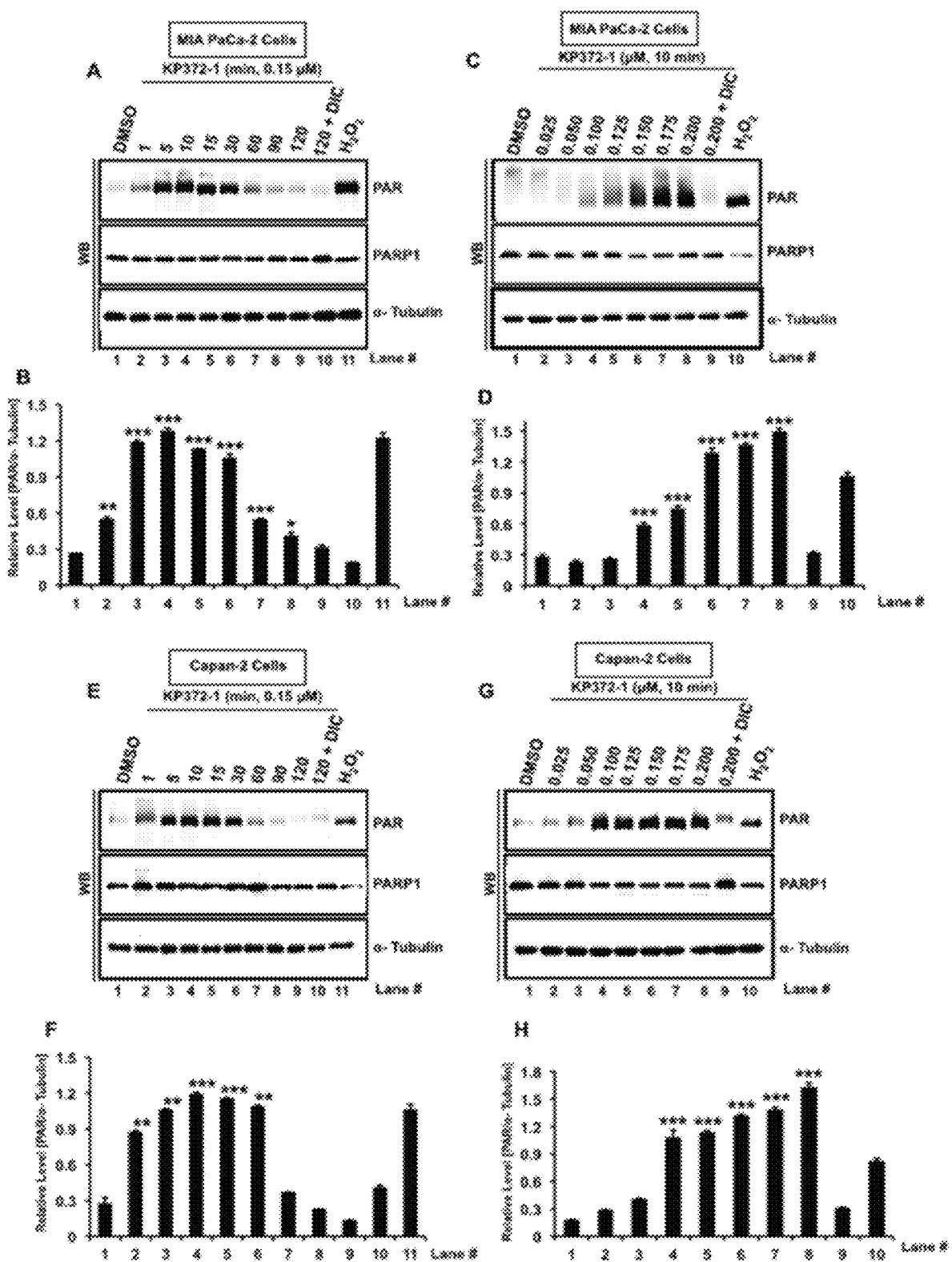
FIG. 6 PANEL A-PANEL H show that KP372-1 hyperactivates PARP1 in pancreatic cancer cells. (PANEL A-PANEL H) Assessment of PAR (poly-(ADP-ribose)) via Western blotting as a marker of PARP1 hyperactivation by KP372-1-induced DNA damage. MIA PaCa-2 cells treated with 0.15 μM KP372-1±50 μM DIC for indicated time (min) points (PANEL A-PANEL B), blot image and quantification, respectively, and with indicated dose of KP372-1 (μM)±50 μM DIC for 10 min (PANEL C-PANEL D), blot image and quantification, respectively. Capan-2 cells treated with 0.15 μM KP372-1±50 μM DIC for indicated time (min) points (PANEL E-PANEL F), blot image and quantification, respectively, and with indicated dose of KP372-1 (μM)±50 μM DIC for 10 min (PANEL G-PANEL H), blot image and quantification, respectively. Representative Western blot images are presented. Bar graphs represent quantification of band intensities (means±SEM) of PAR normalized to α-tubulin of respective sample from n=5. Band intensities were detected by ImageJ software (version 1.53c, imagej.net) and α-tubulin was used as loading control. Cell lysates prepared from $H_2O_2$-treated cells (1 mM, 15 min in 1×PBS) served as positive control. p values were obtained via two-tailed student's t-tests. *, $p<0.05$; , $p<0.01$; *$p<0.001$, comparing treated with control (DMSO) samples. WB; Western blot.

Time-course and dose-response studies were carried out to assess poly(ADP-ribose) (PAR) formation using Western blotting as a measure of PARP1 hyperactivation. Cell lysate obtained from $H_2O_2$ treated cells were utilized as positive control. Dramatic elevation in PAR formation was observed at multiple time points within a 2 h window in MIA PaCa-2 cells treated with 0.15 µM KP372-1, where co-treatment with DIC brought down PAR formation similar to DMSO treated control cells (FIG. 6 PANEL A and PANEL B). Next, dose-response experiments were conducted with 10 min KP372-1 treatment. A dose-dependent enhancement of PAR formation was observed (FIG. 6 PANEL C and PANEL D). To validate further PARP1 hyperactivation by KP372-1 treatment, similar studies were carried out in Capan-2 cells. Time- and dose-dependent induction of PAR formation in Capan-2 cells were observed (FIG. 6 PANEL E-PANEL H) similar to that of MIA PaCa-2 cells. NQO1-deficient PANC-1 cells treated with similar conditions did not exhibit increased PAR signal above background levels (FIG. 10C PANEL E). These data show that KP372-1 treatment induces PARP1 hyperactivation in NQO1-expressing pancreatic cancer cells.

Example 6: KP372-1 Treatment Activates Caspase-3 in Pancreatic Cancer Cells

Figure 7:
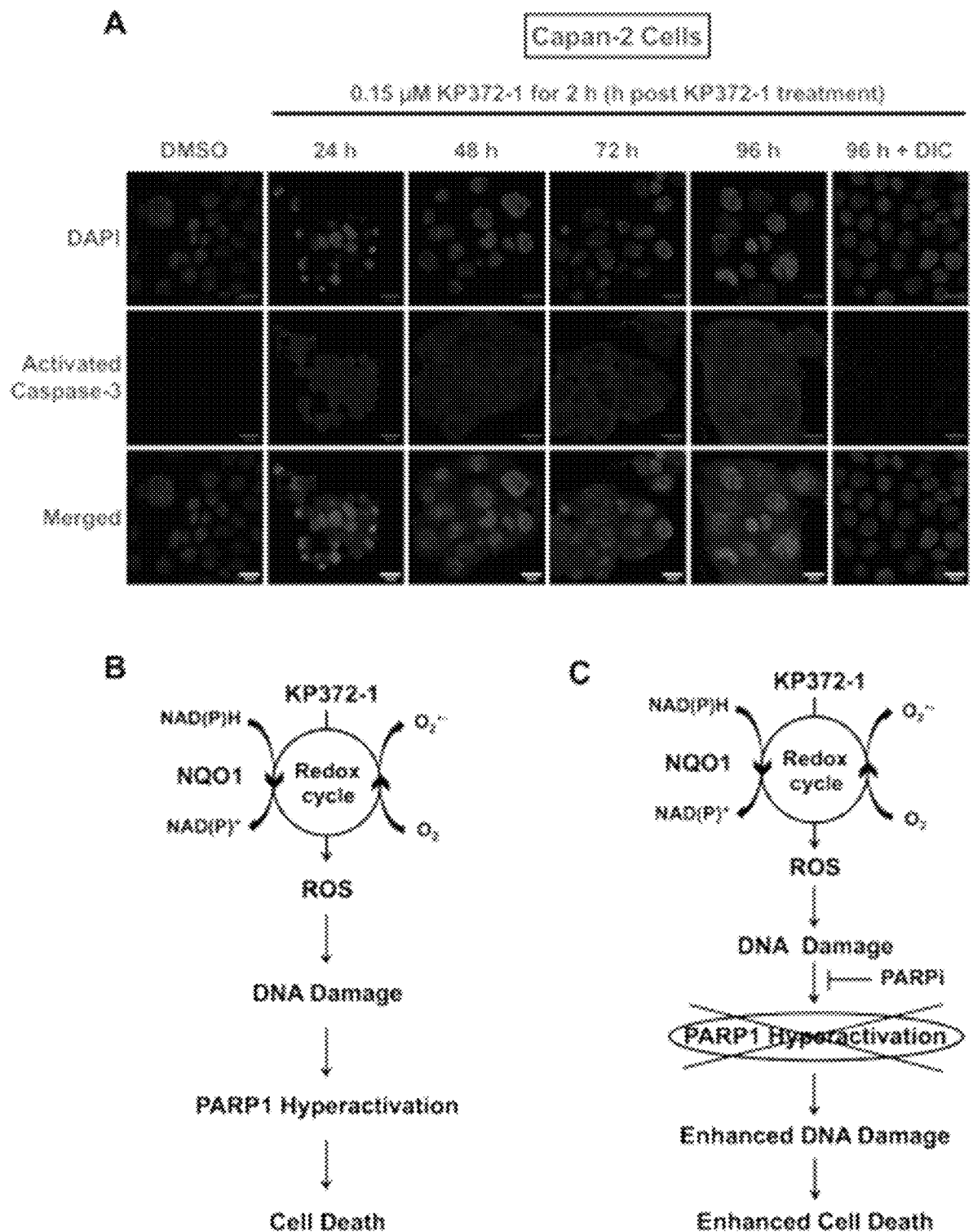
FIG. 7 PANEL A-PANEL C show that KP372-1 treatment activates caspase-3 in pancreatic cancer cells. (PANEL A) Evaluation of caspase activation via confocal immunofluorescence microscopy using cleaved caspase-3 antibody (i.e., activated caspase-3). Capan-2 cells were treated with 0.15 μM KP372-1±50 μM DIC for 2 h and released for indicated time points (h) prior to processing for immunofluorescence. Note strong staining of capan-2 cells with activated caspase-3 from 24-96 h, whereas, DMSO treated cells do not show appreciable signal. Representative image from n=4 biological repeats has shown. (PANEL B-PANEL C) Model providing mechanistic insight into cellular consequences of KP372-1 exposure to NQO1 overexpressing cancer cells.

To gain insight into cell death pathway instigated in pancreatic cancer by KP372-1 treatment, caspase activation was studied using immunofluorescence confocal microscopy with an antibody specific to cleaved caspase-3 (i.e., activated caspase-3). Capan-2 cells were treated with 0.15 µM KP372-1 for 2 h and released for indicated time points prior to fixing, incubating with antibodies and image acquisition. Compared to control (DMSO-treated) cells, KP372-1 treated cells clearly showed enhanced signal for activated caspase-3 at all the time points within 24-96 h window (FIG. 7 PANEL A). DIC treatment blocked KP372-1-induced activation of caspase-3 (FIG. 7 PANEL A). Collectively, these findings suggest that KP372-1 treatment leads to caspase-3 activation in pancreatic cancer cells to initiate cell death.

Based on data presented in FIGS. 1A-1C, FIGS. 2A-2B, FIGS. 3A-3B, FIG. 4, and FIGS. 5A-5B, the model presented in FIG. 7 PANEL B was developed for KP372-1-induced cytotoxicity, where NQO1-dependent redox cycling generates ROS that cause DNA damage. To counteract DNA damage, cells hyperactivate PARP1 in an attempt to repair the damage. However, the amount of DNA damage at higher doses of KP372-1 exhausts the cellular DNA repair capacity, and cells activate caspase-3 to initiate cell death (FIG. 7 PANEL B). Induction of DNA damage by KP372-1 with simultaneously blocking PARP1 activity is expected to lead to augmented DNA damage and cause enhanced cell death at lower doses of KP372-1 (FIG. 7 PANEL C).

Figure 8:
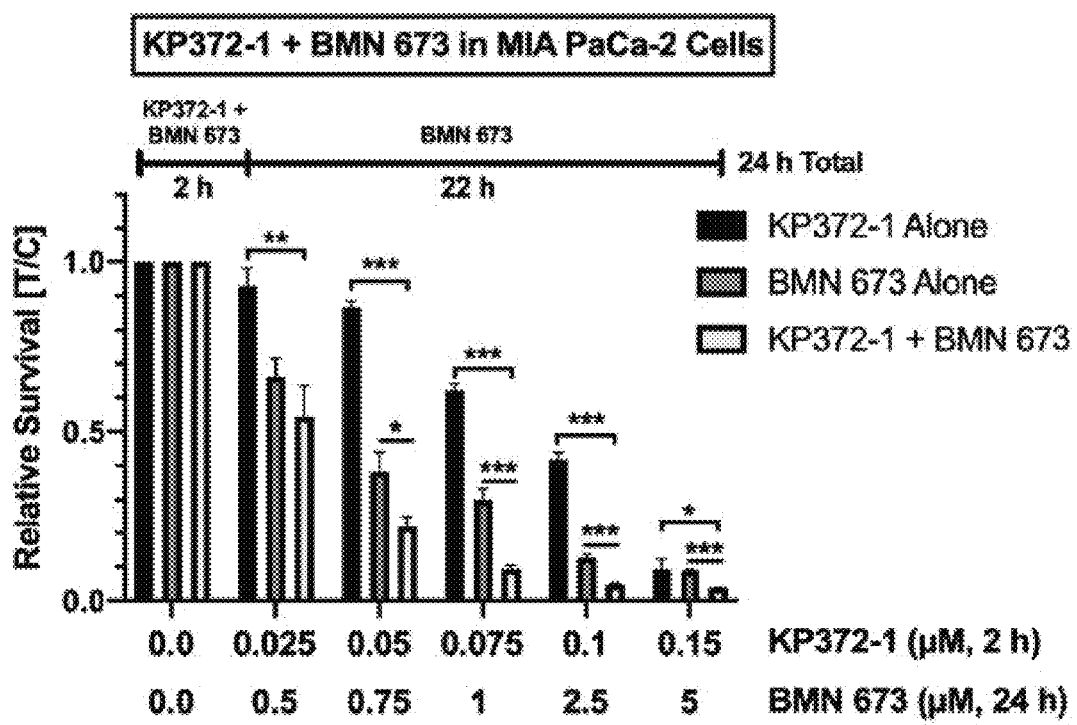
FIG. 8 PANEL A-PANEL B show that KP372-1 and PARP1 inhibition combination enhances cytotoxicity of pancreatic cancer cells. Relative survival measured by DNA content assay in the presence of indicated μM concentrations of KP372-1±BMN 673 (PARP1/2 inhibitor). (PANEL A) MIA PaCa-2 cells were treated with BMN 673 and KP372-1 in the order indicated by outline mentioned on the top part of the graph. Bar graph represent means±SEM for individual or combination treatment over control (i.e., DMSO) treated (T/C) samples from n=3, each in triplicate. p values were obtained via two-tailed student's t-tests. *, $p<0.05$; , $p<0.01$; *, $p<0.001$, comparing combination with individual treatments. (PANEL B) Dose reduction index (DRI) values were calculated using the survival data from panel A as input via CompuSyn 1.0 software where any value above 1 shows reduction in dose for individual agents to achieve given fraction affected (Fa) upon combination. p values were obtained via two-tailed student's t-tests. *, $p<0.05$; , $p<0.01$; *, $p<0.001$, comparing the dose reduction value to the additive value of 1.
Figure 8:
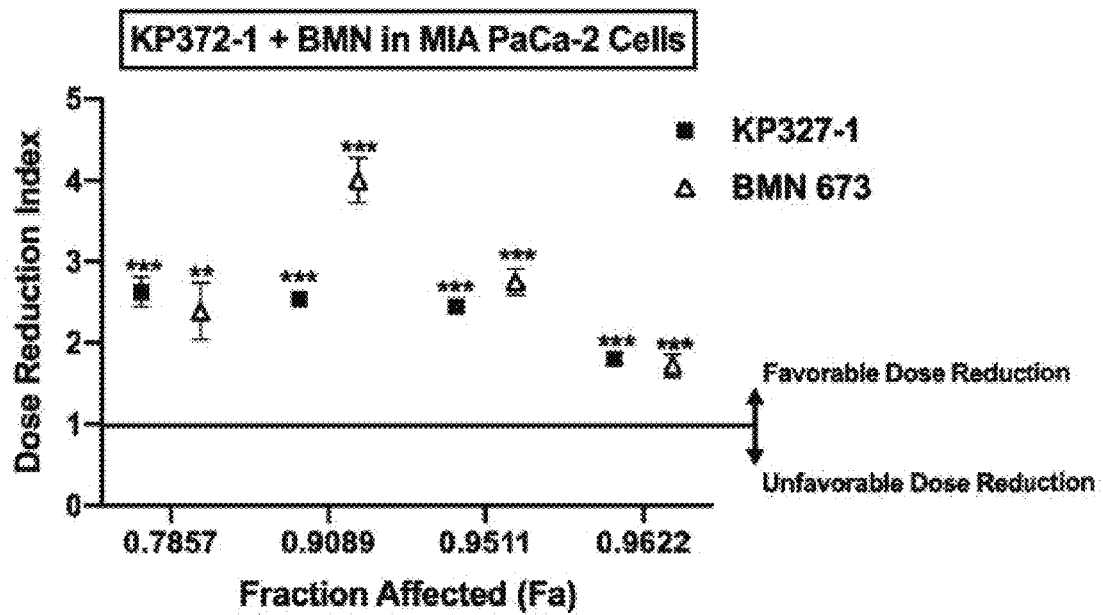

Example 7: Combination of KP372-1 and PARP Inhibition Enhances KP372-1-Induced Cytotoxicity in Pancreatic Cancer Cells Observed PARP1 hyperactivation in response to KP372-1 treatment (FIG. 6) suggested that pancreatic cancer cells rely on PARP1 activity to counteract cellular stress created by KP372-1. Thus, blocking of PARP1 activity in addition to KP372-1 treatment was expected to augment cytotoxicity of pancreatic cancer cells further (FIG. 7 PANEL C). Cell survival studies were conducted with a potent FDA-approved PARP inhibitor, BMN 673 (talazoparib), in combination with KP372-1. Significant enhancement of cytotoxicity of MIA PaCa-2 cells with multiple doses of KP372-1+BMN 673 in combination was observed compared to either of the agents alone (FIG. 8 PANEL A). To gain further insight into effectiveness of combination treatment, data of FIG. 8 PANEL A was used as input and calculated the dose reduction index (DRI) values as a function of fraction affected (Fa). The combination of KP372-1 and BMN 673 resulted in favorable dose reductions of both compounds, providing additional evidence that the combination treatment is more effective than single agents alone (FIG. 8 PANEL B). For example, to achieve Fa=0.9 in combination, only 0.075 µM KP327-1 and 1 µM BMN 673 is required (FIG. 8 PANEL A), which correlated to a favorable DRI value of 2.53 for KP327-1 and 3.99 for BMN 673 (FIG. 8 PANEL B). Finally, the combination index (CI) values and associated descriptions further support the effectiveness of KP372-1+BMN 673 (TABLE 1).

TABLE 1 shows the combination index values for MIA PaCa-2 cells treated with KP372-1 and BMN 673. The combination index values (CI) for MIA PaCa-2 cells treated with KP372-1 and BMN 673 in FIG. 8 PANEL A displayed as CI±S.D. with accompanying synergy description. All values display synergy to nearly additive combination index values. The strongest synergy was observed at a dose of 0.075 µM KP372-1 in combination with 1 µM BMN 673. Collectively, these data suggest that combination of KP372-1 with the FDA-approved PARP inhibitor BMN 673 induces enhanced cell death in pancreatic cancer cells.

TABLE 1

| KP372-1 dose (µM) | BMN 673 dose (µM) | Fraction affected (Fa) | Combination index (CI) | Synergy description |
|---|---|---|---|---|
| 0.025 | 0.5 | 0.5224 ± 0.03 | 1.061 ± 0.09 | Nearly additive |
| 0.05 | 0.75 | 0.7857 ± 0.03 | 0.808 ± 0.09 | Moderate synergism |
| 0.075 | 1 | 0.9089 ± 0.007 | 0.646 ± 0.03 | Synergism |
| 0.1 | 2.5 | 0.9511 ± 0.003 | 0.775 ± 0.03 | Moderate synergism |

Example 8: KP372-1 Sensitizes a Broad Range of Cancer Cells

Figure 12:
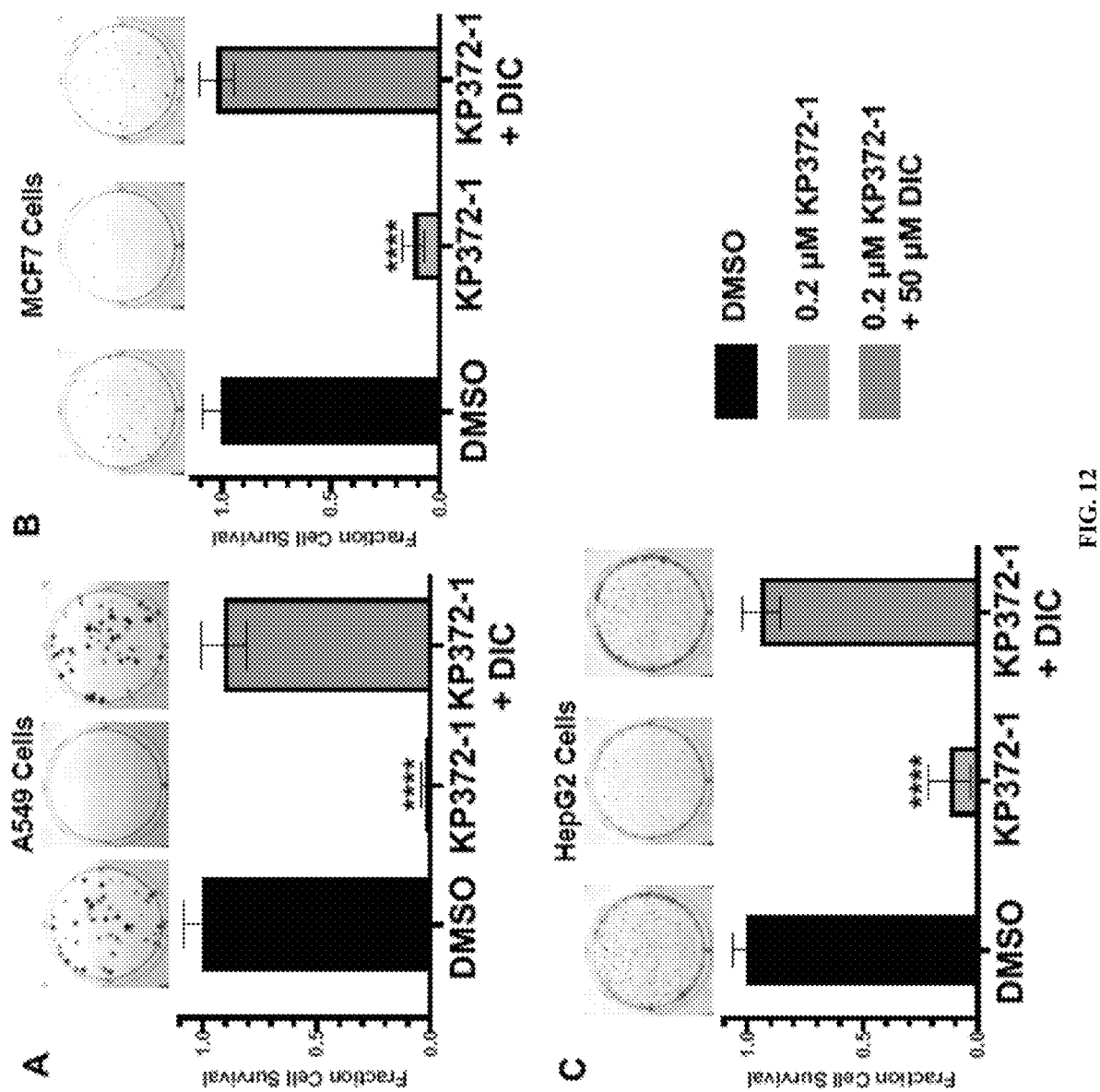
FIG. 12 PANEL A-PANEL C shows that KP372-1 sensitizes lung, breast and liver cancer cells. (PANEL A-PANEL C) Relative clonogenic survival (Means±SEM from n=3) of A549 lung adenocarcinoma cells (PANEL A), MCF7 breast adenocarcinoma cells (PANEL B) and HepG2 liver carcinoma cells (PANEL C) in the presence of DMSO or 0.2 μM KP372-1±50 μM DIC for 2 h. p values were obtained via an ordinary, one-way ANOVA using the Dunnett's multiple comparisons test. ****, p<0.0001.

To test a broader applicability of KP372-1, we evaluated sensitivity of various cancer cells against KP372-1 using colony forming assay. Briefly, A549 lung adenocarcinoma cells, MCF7 breast adenocarcinoma and HepG2 liver carcinoma cells were exposed to vehicle control (DMSO), 0.2 µMKP372-1 and 0.2 µM KP372-1+50 µM Dicoumarol (DIC, competitive inhibitor of NQO1 enzyme) for two hours, then media were replaced and cells were allowed to grow the colonies in fresh media for approximately two weeks. Next, colonies were stained with crystal violet, quantified and clonogenic fraction cell survival data relative to control were plotted with inclusion of representative images of colonies from different treatment groups. Control treatment showed clearly visible colonies but KP372-1 treatment significantly reduced cell survival of lung, breast and liver cancer cell lines, A549, MCF7 and HepG2, respectively, and NQO1 inhibition by DIC treatment restored the survival of these cells (FIG. 12). Collectively, these data demonstrate that KP372-1 sensitizes a wide variety of cancer cells in an NQO1 dependent manner. Since majority of solid cancers overexpress NQO1, therefore, KP372-1-induced cytotoxicity offers a potent and promising chemotherapeutic strategy against cancer.

Example 9: KP372-1 as an Inhibitor of PDK1/Akt Signaling

Figure 11:
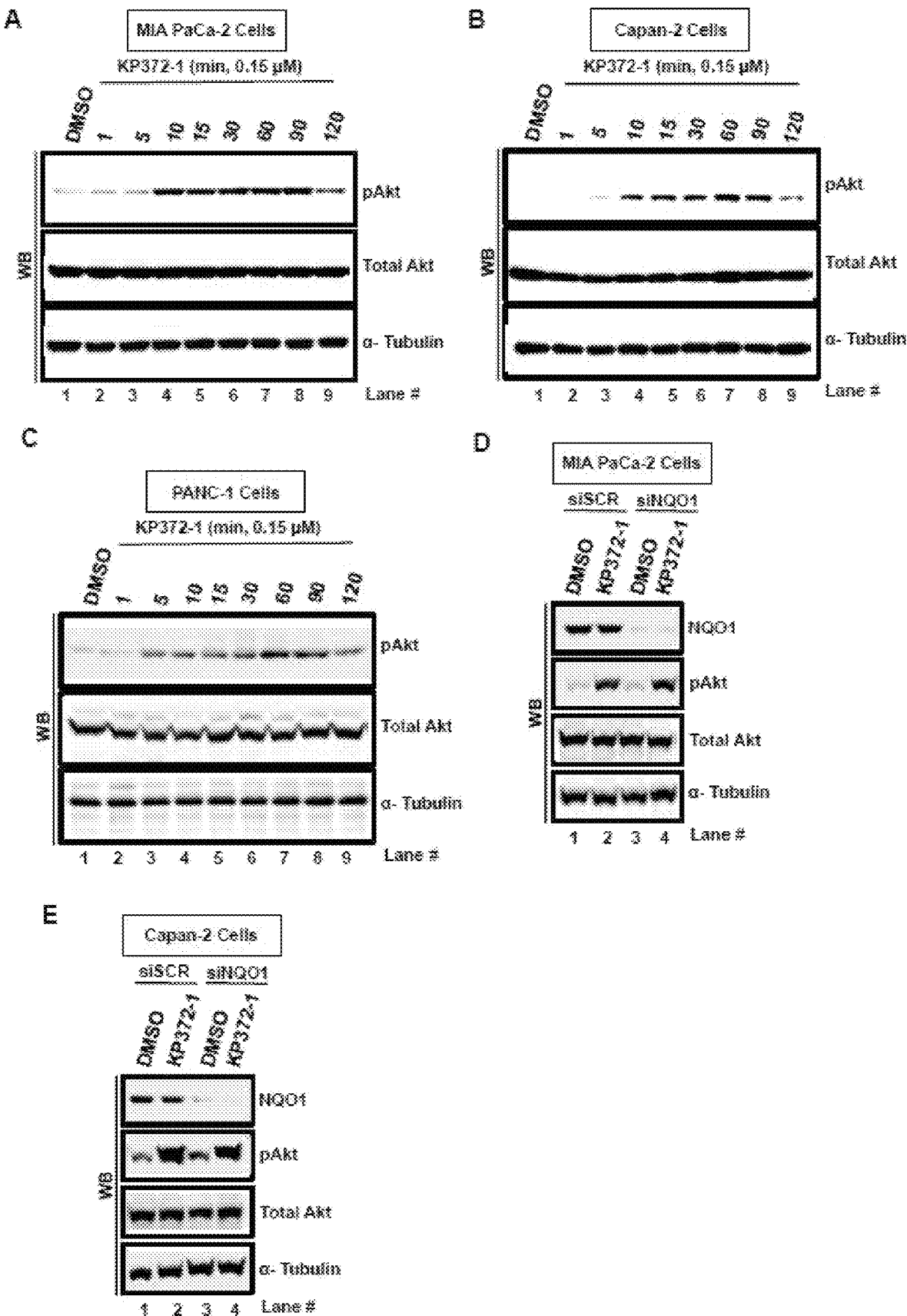
FIG. 11 PANEL A-PANEL E shows that KP372-1 promotes Akt phosphorylation independent of NQO1 expression. Assessment of phosphorylated Akt (pAkt) via Western blotting induced by KP372-1. (PANEL A) MIA PaCa-2 cells treated with 0.15 μM KP372-1 for indicated time (min) points. (PANEL B) Capan-2 cells treated with 0.15 μM KP372-1 for indicated time (min) points. (PANEL C) PANC-1 cells treated with 0.15 μM KP372-1 for indicated time (min) points. (PANEL D) MIA PaCa-2 cells+siSCR or siNQO1 treated with 0.15 μM KP372-1 for 15 min. (PANEL E) Capan-2 cells+siSCR or siNQO1 treated with 0.15 μM KP372-1 for 15 min. Representative Western blot images are shown here from n=4.

Initial studies reported KP372-1 as an inhibitor of PDK1/Akt signaling pathways compromising cell proliferation and promoting apoptosis. The data show transiently increased Akt phosphorylation in pancreatic cancer cells treated with KP372-1 (FIG. 11). However, Akt phosphorylation induced by KP372-1 treatment was independent of NQO1 status, since Akt phosphorylation remains intact in MIA PaCa-2 and Capan-2 cells treated with KP372-1 after siRNA-mediated knockdown of NQO1 (FIG. 11). Also, despite exhibiting strong Akt phosphorylation comparable to that of MIA PaCa-2 and Capan-2 (S3), naturally NQO1-deficient PANC-1 cells (FIGS. 1A-1C) showed no toxicity against KP372-1 (FIGS. 2A-2B, FIGS. 9A-9B, FIGS. 1A-1C, FIG. 11). Furthermore, NQO1-depleted MIA PaCa-2 showed no sensitivity to KP372-1 despite maintaining the intact Akt-phosphorylation, (FIGS. 2A-2B and FIG. 11). Collectively, these observations show that cytotoxicity instigated by KP372-1 is independent of Akt phosphorylation.

Example 10: Materials and Methods

Chemicals: KP372-1, β-lapachone (β-lap), dicoumarol (DIC), N-acetylcysteine amide (NAC), 3-(4,5-dimethylthiazol-2-yl)-2,5-diphenyltetrazolium bromide (MTT), Phenylarsine oxide (PAO) and Hoechst 33258 dye were purchased from Sigma-Aldrich. KP372-1 was also purchased from Echelon Biosciences Inc. BMN 673 (Talazoparib) was purchased from Selleck Chemicals LLC.

Antibodies and siRNA: NQO1 (A180), PARP1 (F-2), total Akt (B1), anti-rabbit IgG-HRP (sc-2030) antibodies, and siNQO1 were purchased from Santa Cruz Biotechnology. γH2AX (Clone JBW301) and anti-mouse IgG-HRP (AP160P) antibodies were obtained from EMD Millipore. Cleaved caspase-3 and phosphoAkt antibodies were purchased from Cell Signaling Technology. PAR (4335-MC) antibodies were obtained from Trevigen. Non-target control siRNA (siSCR) and α-tubulin (T9026) antibodies were purchased from Sigma-Aldrich.

Oncomine data acquisition: Pancreatic cancer mRNA expression profile data sets were downloaded from a public database, ONCOMINE. Data sets were used directly without further processing or normalization.

Cell culture and siRNA transfection: All of the pancreatic cancer cell lines used in the study were gifted by the Der lab at the University of North Carolina, Chapel Hill. MIA PaCa-2 and PANC-1 cells were maintained in DMEM supplemented with L-glutamine and 10% FBS. AsPC-1 and BxPC-3 cells were maintained in RPMI 1640 supplemented with 10% FBS. Capan-2 cells were maintained in McCoy's 5A media supplemented with 10% FBS. Finally, hTERT-HPNE cells were maintained in 75% DMEM and 25% Medium M3 Base supplemented with 5% FBS, 10 ng/mL human recombinant EGF, 5.5 mM D-glucose (1 g/L), and 750 ng/mL puromycin. All cells were kept in a 37° C. incubator and 5% $CO_2$. Cells were routinely monitored to confirm the absence of mycoplasma contamination.

For transient transfections, OptiMEM, Lipofectamine 2000 RNAiMax, siSCR, siNQO1 were used. Typical transfection experiments were done in 6-well plates (200,000 cells/well) using two sequential transfections to ensure higher efficiency of knockdown, each with 25 nM siRNAs for a total of 72 h. For experiments describing cell survival after NQO1 knockdown, plating and treatment with KP372-1 were completed within 72 h of the first transfection.

Western blotting: For a typical Western blotting experiment, ~$1 \times 10^6$ cells were seeded in 35 mm dishes and allowed to adhere overnight. The next day, where appropriate, cells were treated with indicated concentrations (µM) of KP372-1 or KP3721+dicoumarol (DIC) for the specified time points and $H_2O_2$ treatment (1 mM, 15 min in 1×PBS) was used as positive control. Cells were then lysed in ice-cold RIPA buffer supplemented with 1× protease and 1× phosphatase inhibitors. Whole-cell extracts were sonicated, spun by centrifuge at 13,000 rpm and supernatants were collected. Protein concentrations of supernatants were determined by the BCA assay. Proteins (15-20 µg) were separated by SDS-PAGE gels and transferred to nitrocellulose membranes. The blots were then blocked in either 1× casein blocking buffer or in 5% Skim Milk-TB ST and incubated with primary antibodies followed by appropriate secondary antibody conjugated with HRP. Protein bands were detected by SuperSignal West Pico PLUS Chemiluminescent Substrate and imaged on an Azure c600. Blot images were adjusted for brightness and contrast, and were cropped to make final figures. For quantification of western blots, protein band intensities were analyzed using NIH ImageJ software (version 1.53c, imagej.net) and specific protein band intensities were normalized to the loading control. The reported relative intensities are the results of n>3.

Cell Survival Assays

DNA content assay: A modified cell survival assay measuring DNA content over ~7-day period was utilized. Cells were seeded at 10,000 cells/well in 48-well plates in 0.5 mL of media. The next day, media were aspirated and replaced with 0.5 mL media containing the indicated concentrations of KP372-1 (µM) alone or in combination with 50 µM DIC. The cells were exposed for 2 hours (2 h) and the media were again aspirated and replaced with fresh media (without KP372-1). The cells were then allowed to grow for ~7 days or until control samples became confluent. Cells were then lysed in 250 µl dI water, then freeze-thawed followed by suspension in 0.5 mL 1× TNE buffer containing Hoechst 33258 fluorescent dye. The DNA content was determined by measuring florescence signal using a Victor X5 plate reader. Fluorescence values of treated samples were normalized to that of control samples and plotted as means±SEM for treated over control (i.e., DMSO) treated (T/C) samples. The reported values are the results of the following sample sizes for KP372-1±DIC: MIA PaCa-2 concentration (n=5); Capan-2 concentration (n=3); MIA PaCa-2±siSCR/siNQO1 (n=3); hTERT-HPNE (n=3); PANC-1 (n=3); AsPC-1 (n=4); BxPC-3 (n=3); MIA PaCa-2 time (n=3); Capan-2 time (n=3). The reported values are the results of the following sample sizes for β-lap±DIC: MIA PaCa-2 (n=4) and Capan-2 (n=4).

Colony forming assay: MIA PaCa-2 or PANC-1 cells were seeded on 6-well plates at 250, 100, or 50 cells per well. The next day, cells were treated with vehicle (0.05% DMSO), 0.15 µM KP372-1, or 0.15 µM KP372-1 with 50 µM DIC for 2 h. The media was then replaced with fresh media and the cells were allowed to grow for 10 days. Next, the media was removed, and the colonies were fixed and stained with crystal violet solution containing 1× PBS, 1% formaldehyde, 1% methanol, and 0.05% w/v crystal violet for 20 minutes (min). The dishes were thoroughly rinsed in water and allowed to air dry. Colonies containing >50 normal looking cells were and data (means±SD) were expressed as treated/control (T/C) from experiments performed at least three times in triplicate. p values were obtained using an ordinary one-way ANOVA with Dunnett's multiple comparisons test. The reported values are the results of n=4.

MTT assay: MIA PaCa-2, Capan-2, or PANC-1 cells were seeded in 96-well plates (4,000 cells/well) and adhered overnight. The next day, cells were treated with the indicated concentrations of KP372-1, 50 µM DIC, or KP372-1+50 µM DIC for 2 h, followed by replacement with fresh media, and the cells were allowed to recover for 48 h. Phenylarsine oxide (PAO) was used as a positive control at a final concentration of 100 µM and 0.2% DMSO was used as a negative control. Following the 48 h recovery, 20 µL of MTT solution (5 mg/mL in 1× PBS) was added to each well and cells were incubated at 37° C. for 2 h. The supernatants were aspirated and 100 µL of DMSO was added to each well to dissolve the formazan crystals. Absorbance was then measured using a Victor X5 plate reader. Data (% means±S.D.) were expressed as treated/control values from three biological replicates. The reported values are the results of n=4. p values were obtained using an ordinary one-way ANOVA with Dunnett's multiple comparisons test.

Reactive oxygen species (ROS) measurement: For the detection of $H_2O_2$ production, a ROS-Glo $H_2O_2$ assay kit was used according to manufacturer's recommendation with the indicated changes. Briefly, 15,000 cells/well were seeded in 96-well white-walled plates with clear bottoms and cells were allowed to adhere overnight. The following day, cells were treated with indicated concentrations (µM) of KP372-1 or KP372-1+DIC or KP372-1+N-acetylcysteine amide (NAC, 1 mM or 5 mM for total of 5 h (pre-treatment for 3 h and co-treatment for 2 h)) or DMSO (as control) for specified time (min) points in a total volume of 50 µl that contained 10 µL of $H_2O_2$ substrate. Then, 50 µl of ROS-Glo detection solution was added to each well and cells were incubated for 20 min at room temperature. Luminescence was measured using a Victor X5 plate reader. Luminescence values of treated samples were normalized to luminescence values of control samples to generate reported graphs. The reported values are the results of n=4.

8-oxoguanine (8-oxoG) measurement: Cells were seeded on 6-well plates (~200,000 cells/well) containing glass slides and adhered overnight. The next day, cells were treated with indicated concentrations (µM) of KP372-1 or KP372-1+DIC or KP372-1+N-acetylcysteine amide (NAC, 5 mM for total of 4 h (pre-treatment for 3 h and co-treatment for 1 h)) or DMSO (as control) for 1 h. Cells treated with $H_2O_2$ (1 mM, 15 min in 1×PBS) served as positive control. Afterwards, media were replaced with fresh media (without KP372-1).

A standard immunofluorescence microscopy protocol was used. Cells were gently washed in 1×PBS, followed by fixation with ice-cold methanol: acetic acid (3:1, v/v) overnight at −20° C. Fixed cells were gently washed in 1×PBS at room temperature (3×, 5 min each) followed by incubation in blocking solution (1× PBS containing 5% normal goat serum) for 1 h at room temperature. Next, the cells were incubated with 8-oxoG primary antibody (1:2,000 dilution in 1×PBS containing 5% normal goat serum) for 1 h at room temperature. The cells were then washed (3×, in 1× TBST followed by 1× in PBST, 5 min each) and incubated with Alexa Fluor 594 fluorescent secondary antibody (1:2,000 dilution in 1×PBS containing 5% normal goat serum) for 1 h at room temperature. The cells were then washed (3×, in 1× TBST followed by 1× in PBST, 5 min each). Finally, the wash buffer was removed, and the cover glass was mounted with prolong gold antifade mounting medium with DAPI (nuclear stain). Images were acquired using Olympus FV10i confocal laser scanning microscope with 60× oil immersion objective. The images were analyzed and quantified using NIH Image) software (version 1.53c, imagej.net). Reported data is representative of n=4, each in duplicate from total of 150 cells. p values were obtained using an ordinary one-way ANOVA with Dunnett's multiple comparisons test.

Neutral comet assay: For the neutral comet assay, the Comet Assay Kit was used according to manufacturer's recommendation with the indicated changes. MIA PaCa-2 cells were plated on 6-well plates and adhered overnight. The next day, cells were treated for 1 h with vehicle control (0.05% DMSO), 0.15 µM KP372-1, 0.15 µM KP372-1 with 50 µM DIC, or 0.15 µM KP372-1 with N-acetylcysteine amide (NAC, 5 mM for total of 4 h (pre-treatment for 3 h and co-treatment for 1 h)). 1 mM $H_2O_2$ in PBS treated for 15 min was used as a positive control. Cells were trypsinized and collected, washed with PBS, and resuspended in PBS at a concentration of 2×105 cells/mL. Cells were added to melted LMAgarose cooled to 37° C. at a ratio of 1:10 and pipetted onto a pre-warmed comet slide and spread evenly. Slides were then placed at 4° C. for 30 min to allow adherence of the agarose to the slides. The slides were then gently immersed in lysis solution overnight at 4° C. Following lysis, the slides were immersed in 1× Neutral Electrophoresis Buffer containing tris base and sodium acetate (corrected to pH 9 with glacial acetic acid) for 30 min at 4° C. The slides were then electrophoresed at 20 volts for 45 min at 4° C. in the neutral electrophoresis buffer. Next, the slides were gently immersed in DNA precipitation solution containing 1 M ammonium acetate in 95% ethanol for 30 min at room temperature followed by immersion in 70% ethanol for 30 min at room temperature. The slides were then dried at 37° C. for 10 min and subsequently stained with a 1:25,000 dilution of SYBR Green in TE buffer (10 mM Tris-HCl pH 7.5 with 1 mM EDTA) for 30 min at room temperature in the dark. Slides were rinsed briefly with distilled water twice and then allowed to fully dry before imaging. Images were acquired using an Olympus FV10i confocal laser scanning microscope with a 10× objective. The comets were analyzed using the ImageJ (version 1.53c, imagej.net) plug-in OpenComet v1.3 (www.biocomet.org) and the tail moment was normalized to the DMSO control (n=100 comets per sample). p values were obtained using an ordinary one-way ANOVA with Dunnett's multiple comparisons test.

Confocal immunofluorescence microscopy: Cells were seeded on 6-well plates (~100,000 cells/well) containing glass slides and allowed to adhere overnight. The next day, cells were treated with DMSO or KP372-1 (0.15 µM) for 2 h. Afterwards, media were replaced with fresh media (without KP372-1). Then, cells were fixed at indicated time points (24, 48, 72, and 96 h) by gentle washing in 1×PBS, followed by fixation with ice-cold methanol: acetic acid (3:1, v/v) overnight at 20° C. Fixed cells were gently washed in 1×PBS at room temperature (3×, 5 min each). The cells were then incubated in blocking solution (1× PBS containing 5% normal goat serum) for 1 h at room temperature. Then, the cells were incubated with cleaved caspase-3 (i.e., activated caspase) primary antibody (1:500 dilution in 1×PBS containing 5% normal goat serum) for overnight at 4° C. The next day, the cells were washed (3×, 5 min each in 1×PBS) and incubated with Alexa Fluor 594 fluorescent secondary antibody (1:1000 dilution in 1×PBS containing 5% normal goat serum) for 1 h at room temperature. The cells were then washed (3×, 5 min each in 1×PBS). Finally, the wash buffer was removed, and the cover glass was mounted with prolong gold antifade mounting medium with DAPI (nuclear stain). Images were acquired using Olympus FV10i confocal laser scanning microscope with a 60× oil immersion objective.

Synergy calculations: Drug synergy was calculated using CompuSyn 1.0 software (www.combosyn.com). MIA PaCa-2 cells (4,000 cells/well) were seeded in 96-well plates and treated with KP372-1 (2 h) or BMN 673 (24 h) alone to determine the $IC_{50}$ values of each drug alone. Cells were treated with a non-constant combination of KP372-1 and BMN 673 for 2 h and replaced with media containing the same concentrations of BMN 673 for additional 22 h (24 h total). Then, cell survival was assessed via DNA content assay similarly to as described above. Relative survival was plotted to obtain Fraction affected (Fa) values. Fa values were normalized to the DMSO control and entered into CompuSyn. Dose-Reduction Index (DRI) values were calculated using the Chou-Talalay method. Briefly, DRI values are calculated using the following equation:

$$DRI = (D_x)_1 / (D)_1$$

where $(D_x)_1$ is the dose of the drug alone and $(D)_1$ is the dose of the drug in combination. DRI values are defined as favorable (DRI>1) or unfavorable (DRI<1). Reported values are the results of n=3.

Statistical analysis: Unless otherwise stated, data (mean±SEM) were graphed and two-tailed Student's t tests using the Holm-Sidak method to correct for multiple (more than one) comparisons were performed. For the 8-oxoG experiments, the neutral comet assay, and colony forming assays, an ordinary one-way ANOVA was used to compare treated samples to control. The minimum biological replicate size was n=3. Alpha was set to 0.05. GraphPad Prism 8 was used to perform statistical analyses. Images are representative results of experiments performed with n>3 biological repeats. *p<0.05; p<0.01; *p<0.001; ****p<0.0001.

EMBODIMENTS

The following non-limiting embodiments provide illustrative examples of the invention, but do not limit the scope of the invention.

Embodiment 1. A method for treating a condition, the method comprising: a) administering to a subject in need thereof a therapeutically-effective amount of a compound of Formula (I) or pharmaceutically-acceptable salt thereof or Formula (II) or a pharmaceutically-acceptable salt thereof:

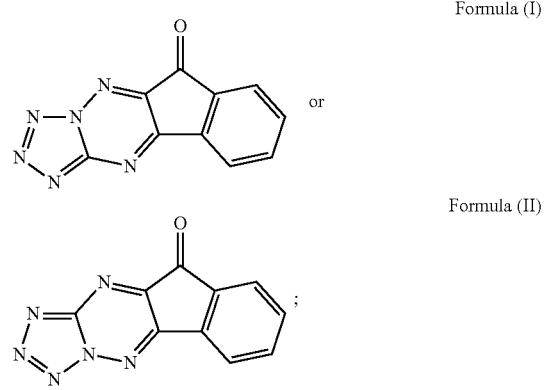

and b) administering to the subject a therapeutically-effective amount of a polymerase inhibitor.

Embodiment 2. The method of embodiment 1, wherein the compound is:

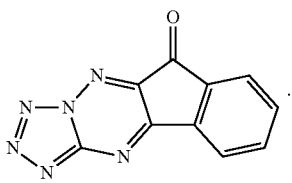

Formula (I)

Embodiment 3. The method of embodiment 1, wherein the compound is:

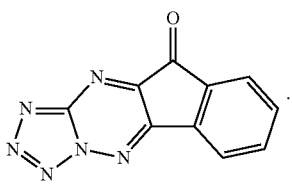

Formula (II)

Embodiment 4. The method of any one of embodiments 1-3, comprising administering the compound of Formula (I) or the pharmaceutically-acceptable salt thereof and the compound of Formula (II) or the pharmaceutically-acceptable salt thereof.

Embodiment 5. The method of any one of embodiments 1-4, wherein the administering of the compound is oral.

Embodiment 6. The method of any one of embodiments 1-4, wherein the administering of the compound is intravenous.

Embodiment 7. The method of any one of embodiments 1-4, wherein the administering of the compound is intratumoral.

Embodiment 8. The method of any one of embodiments 1-7, wherein the therapeutically-effective amount of the compound is from about 50 mg to about 2000 mg.

Embodiment 9. The method of any one of embodiments 1-8, wherein the therapeutically-effective amount of the compound is about 300 mg.

Embodiment 10. The method of any one of embodiments 1-8, wherein the therapeutically-effective amount of the compound is about 600 mg.

Embodiment 11. The method of any one of embodiments 1-8, wherein the therapeutically-effective amount of the compound is about 1200 mg.

Embodiment 12. The method of any one of embodiments 1-11, wherein the condition is a cancer.

Embodiment 13. The method of embodiment 12, wherein the cancer overexpresses NQO1.

Embodiment 14. The method of embodiment 12 or 13, wherein the cancer is pancreatic cancer.

Embodiment 15. The method of embodiment 12 or 13, wherein the cancer is pancreatic ductal adenocarcinoma.

Embodiment 16. The method of embodiment 12 or 13, wherein the cancer is breast cancer.

Embodiment 17. The method of embodiment 12 or 13, wherein the cancer is colon cancer.

Embodiment 18. The method of embodiment 12 or 13, wherein the cancer is cervical cancer.

Embodiment 19. The method of embodiment 12 or 13, wherein the cancer is lung cancer.

Embodiment 20. The method of any one of embodiments 1-19, wherein the administering of the polymerase inhibitor is oral.

Embodiment 21. The method of any one of embodiments 1-19, wherein the administering of the polymerase inhibitor is intravenous.

Embodiment 22. The method of any one of embodiments 1-19, wherein the administering of the polymerase inhibitor is intratumoral.

Embodiment 23. The method of any one of embodiments 1-22, wherein the polymerase inhibitor is a poly ADP ribose polymerase (PARP) inhibitor.

Embodiment 24. The method of any one of embodiments 1-23, wherein the polymerase inhibitor is a PARP1 inhibitor.

Embodiment 25. The method of any one of embodiments 1-23, wherein the polymerase inhibitor is a PARP2 inhibitor.

Embodiment 26. The method of any one of embodiments 23-25, wherein the PARP1 inhibitor is talazoparib or a derivative thereof.

Embodiment 27. The method of any one of embodiments 23-25, wherein the PARP1 inhibitor is talazoparib tosylate.

Embodiment 28. The method of any one of embodiments 1-27, wherein the therapeutically-effective amount of the polymerase inhibitor is from about 0.25 mg to about 1 mg.

Embodiment 29. The method of any one of embodiments 1-27, wherein the therapeutically-effective amount of the polymerase inhibitor is about 0.75 mg.

Embodiment 30. The method of any one of embodiments 1-29, further comprising administering a therapeutically-effective amount of an additional cancer therapy to the subject.

Embodiment 31. The method of embodiment 30, wherein the additional cancer therapy is a chemotherapeutic agent.

Embodiment 32. The method of embodiment 30, wherein the additional cancer therapy is radiotherapy.

Embodiment 33. The method of any one of embodiments 1-32, wherein the subject is human.

What is claimed is:

1. A method for treating cancer, the method comprising:
   a) administering to a subject in need thereof a therapeutically-effective amount of
      i) a compound of Formula (I):

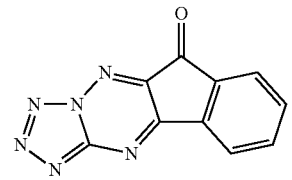

Formula (I)

or pharmaceutically-acceptable salt thereof, or
      ii) a compound of Formula (II):

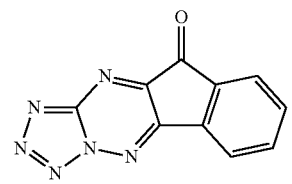

Formula (II)

or a pharmaceutically-acceptable salt thereof; and
   b) orally administering to the subject a therapeutically-effective amount of a poly ADP ribose polymerase (PARP) inhibitor.

2. The method of claim 1, wherein the compound administered is of Formula (I).

3. The method of claim 1, wherein the compound administered is of Formula (II).

4. The method of claim 1, wherein the administering of the compound of Formula (I) or the compound of Formula (II) is oral.

5. The method of claim 1, wherein the therapeutically-effective amount of the compound of Formula (I) or compound of Formula (II) is from about 50 mg to about 2000 mg.

6. The method of claim 1, wherein the cancer overexpresses NQO1.

7. The method of claim 1, wherein the cancer is pancreatic cancer.

8. The method of claim 1, wherein the cancer is breast cancer.

9. The method of claim 1, wherein the cancer is colon cancer.

10. The method of claim 1, wherein the cancer is cervical cancer.

11. The method of claim 1, wherein the cancer is lung cancer.

12. The method of claim 1, wherein the PARP inhibitor is a PARP1 inhibitor.

13. The method of claim 1, wherein the PARP inhibitor is a PARP2 inhibitor.

14. The method of claim 1, wherein the PARP inhibitor is talazoparib or a derivative thereof.

15. The method of claim 1, wherein the PARP inhibitor is talazoparib tosylate.

16. The method of claim 1, wherein the therapeutically-effective amount of the PARP inhibitor is from about 0.25 mg to about 1 mg.

17. A method for treating cancer, the method comprising:
   a) administering to a subject in need thereof a therapeutically-effective amount of a mixture of
      i) a compound of Formula (I):

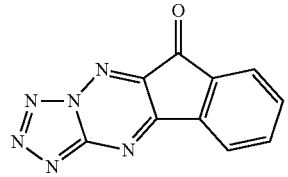

Formula (I)

or pharmaceutically-acceptable salt thereof, and
      ii) a compound of Formula (II):

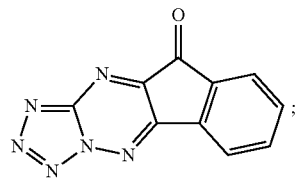

Formula (II)

and
      or a pharmaceutically-acceptable salt thereof; and
   b) orally administering to the subject a therapeutically-effective amount of a poly ADP ribose polymerase (PARP) inhibitor.

18. The method of claim 17, wherein the cancer overexpresses NQO1.

19. The method of claim 18, wherein the cancer is a solid cancer.

20. The method of claim 19, wherein the cancer is selected from the group consisting of lung cancer, colon cancer, breast cancer, and pancreatic cancer.

* * * * *